United States Patent
Lim

(10) Patent No.: US 12,364,779 B2
(45) Date of Patent: Jul. 22, 2025

(54) STERILIZATION APPARATUS AND STERILIZATION METHOD

(71) Applicant: PLASMAPP CO., LTD., Daejeon (KR)

(72) Inventor: Youbong Lim, Daejeon (KR)

(73) Assignee: PLASMAPP CO., LTD., Daejeon (KR)

(*) Notice: Subject to any disclaimer, the term of this patent is extended or adjusted under 35 U.S.C. 154(b) by 123 days.

(21) Appl. No.: 17/577,506

(22) Filed: Jan. 18, 2022

(65) Prior Publication Data

US 2022/0133930 A1  May 5, 2022

Related U.S. Application Data

(63) Continuation of application No. 16/345,128, filed as application No. PCT/KR2017/011385 on Oct. 16, 2017, now Pat. No. 11,253,622.

(30) Foreign Application Priority Data

Oct. 25, 2016 (KR) .......................... 10-2016-0139382

(51) Int. Cl.
*A61L 2/20* (2006.01)
*A61L 2/26* (2006.01)
(Continued)

(52) U.S. Cl.
CPC .................. *A61L 2/20* (2013.01); *A61L 2/26* (2013.01); *A61L 2/28* (2013.01); *A61L 2202/11* (2013.01);
(Continued)

(58) Field of Classification Search
CPC ...... A61L 2/20; A61L 2/26; A61L 2/28; A61L 2/208; A61L 2202/11; A61L 2202/121;
(Continued)

(56) References Cited

U.S. PATENT DOCUMENTS 4,817,800 A * 4/1989 Williams .................. A61L 2/26
141/114
4,937,046 A * 6/1990 Andersen ................ A61L 2/206
422/294

(Continued)

FOREIGN PATENT DOCUMENTS

EP 0782529 B1 9/1995
WO WO-0069475 A1 * 11/2000 ............. A61L 2/186

OTHER PUBLICATIONS

Communication dated Jun. 18, 2020, from the European Patent Office in European Application No. 17864899.4.
(Continued)

*Primary Examiner* — Regina M Yoo
(74) *Attorney, Agent, or Firm* — Sughrue Mion, PLLC

(57) ABSTRACT

The present invention provides a sterilization apparatus and a sterilization method. The sterilization method includes: an operation in which a sterilant injection block for containing a sterilant and providing a sterilant injection path for injecting the sterilant or a vacuum packaging pouch having the sterilant injection block is mounted inside a vacuum chamber; and an operation in which the vacuum chamber is operated in a chamber mode in which the vacuum chamber is used as a sterilization container when only the sterilant injection block is mounted and the vacuum packaging pouch
(Continued)

is operated in a pouch mode in which the vacuum packaging pouch is used as a sterilization container when the vacuum packaging pouch is mounted.

9 Claims, 22 Drawing Sheets

(51) Int. Cl.
*A61L 2/28* (2006.01)
*B65D 81/20* (2006.01)
(52) U.S. Cl.
CPC ..... *A61L 2202/121* (2013.01); *A61L 2202/15* (2013.01); *A61L 2202/181* (2013.01); *B65D 81/20* (2013.01)
(58) Field of Classification Search
CPC ........... A61L 2202/15; A61L 2202/181; A61L 2202/122; A61L 2202/13; A61L 2202/24; A61L 2202/123; A61L 2202/14; B65D 81/20; B65D 81/2023; B65B 31/024; B65B 55/10; B65B 55/18; B65B 2210/06
See application file for complete search history.

(56) References Cited

U.S. PATENT DOCUMENTS

| | | | | |
|---|---|---|---|---|
| 4,938,262 A * | 7/1990 | Williams | ................ | A61L 2/24 141/330 |
| 4,941,518 A * | 7/1990 | Williams | .............. | G01F 11/086 141/7 |
| 5,019,344 A * | 5/1991 | Kutner | ................ | A61L 12/066 422/294 |
| 5,037,623 A | 8/1991 | Schneider et al. | | |
| 5,118,471 A * | 6/1992 | Andersen | ................ | A61L 2/206 422/294 |
| 5,227,132 A * | 7/1993 | Andersen | ................ | A61L 2/20 422/294 |
| 5,407,641 A | 4/1995 | Katschnig et al. | | |
| 5,795,552 A * | 8/1998 | Corby | ................ | A61L 2/26 206/532 |
| 5,897,526 A | 4/1999 | Vaillancourt | | |
| 6,066,294 A | 5/2000 | Lin et al. | | |
| 6,224,828 B1 | 5/2001 | Lin et al. | | |
| 6,279,622 B1 * | 8/2001 | Nguyen | ................ | A61L 2/24 422/298 |
| 7,074,374 B1 * | 7/2006 | Fujii | ................ | A61L 2/26 422/294 |
| 7,309,014 B2 * | 12/2007 | Truong | ................ | A61L 2/24 235/462.01 |
| 7,452,504 B2 * | 11/2008 | Wu | ................ | A61L 2/24 422/33 |
| 7,602,284 B2 * | 10/2009 | Wong | ................ | A61L 2/24 340/568.1 |
| 7,811,530 B2 * | 10/2010 | Morrison | ................ | A61L 2/186 422/292 |
| 8,440,139 B2 * | 5/2013 | Choperena | ................ | A61L 2/26 422/298 |
| 8,696,997 B2 | 4/2014 | Hancock | | |
| 2003/0190257 A1 * | 10/2003 | Halstead | ................ | A61L 2/22 422/301 |
| 2005/0025683 A1 * | 2/2005 | Horacek | ................ | A61L 2/186 422/292 |
| 2008/0166264 A1 * | 7/2008 | Halstead | ................ | A61B 1/123 422/29 |
| 2016/0199258 A1 | 7/2016 | Py | | |

OTHER PUBLICATIONS

Notice of Allowance issued in parent U.S. Appl. No. 16/345,128 mailed Oct. 13, 2021.
Non-Final Office Action issued in parent U.S. Appl. No. 16/345,128 mailed Apr. 21, 2021.

* cited by examiner

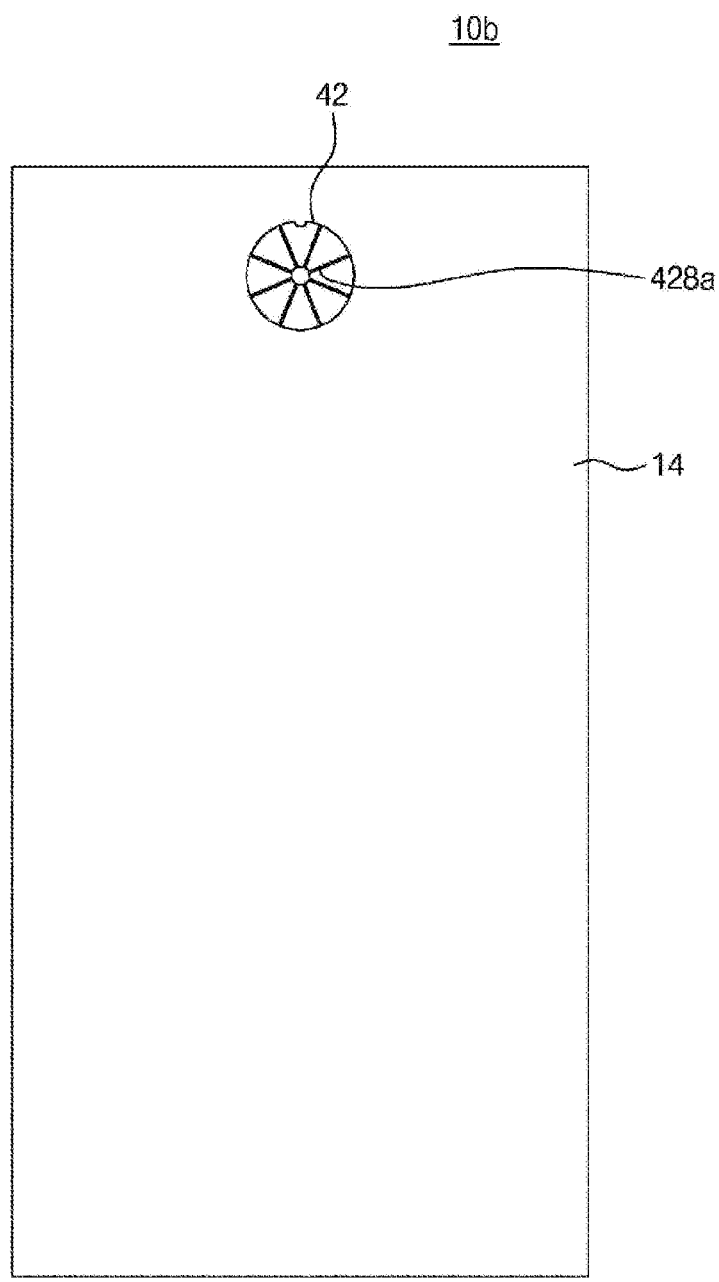

STERILIZATION APPARATUS AND STERILIZATION METHOD

This is a continuation of U.S. application Ser. No. 16/345,128 filed Apr. 25, 2019, which is a National Stage of International Application No. PCT/KR2017/011385, filed Oct. 16, 2017, and claims priority based on Korean Patent Application No. 10-2016-0139382, filed Oct. 25, 2016, in the Korean Patent Office, the contents of which are incorporated by reference in their entirety.

TECHNICAL FIELD

The present invention relates to a sterilization apparatus, and more particularly, to a sterilization apparatus for sterilizing by selectively injecting a sterilant into a vacuum packaging pouch or a vacuum chamber.

BACKGROUND ART

A chemical sterilizer is a device that performs a sterilization process at a low temperature by using a gas such as hydrogen peroxide ($H_2O_2$) and chlorine dioxide ($ClO_2$) as a sterilant.

A conventional chemical sterilizer using $H_2O_2$ as a sterilant forms a base vacuum pressure of 10 Torr or less in a sterilization process chamber and supplies the sterilant. In such a vacuum state, the sterilant may be vaporized at a relatively low temperature (e.g., 60° C.). For sterilization, the vaporized sterilant is supplied into the chamber having a fixed volume. At this time, the supply amount of sterilant needs to be determined so that the sterilant at a set temperature is at or below a maximum pressure (e.g., 30 Torr) at which the sterilant may be maintained in a gaseous state. As such, the sterilant may be transferred to an article to be sterilized in the chamber and the inside of the article only after the sterilant is maintained in the gaseous state, and a successful sterilization process may be performed.

A conventional plasma sterilizer generally has a sterilization chamber of tens of liters or more, and the supply amount of sterilant is at a level of several milliliters in an environment of about 55° C. When a sterilant is injected above a vaporization pressure, partial condensation occurs inside the sterilizer and the sterilizer may not be sufficiently sterilized because it is difficult to sufficiently transfer the sterilant to an article to be sterilized. Also, condensation of the sterilant having a high oxidation property inside or on the surface of the article to be sterilized increases a probability that the sterilant remains on the article to be sterilized even after the process. This results in exposure to a user, which makes it difficult to ensure the safety of the sterilization process. Meanwhile, if a sufficient amount of sterilant is not injected, concentration of the sterilant in the sterilizer is low and sterilization efficiency is low, and successful sterilization is difficult to achieve. Supplying a fixed amount of sterilant is required to ensure the reliability and safety of a sterilization process.

The conventional sterilizer performs a sterilization process in a state in which an article to be sterilized is packaged in a permeable pouch in order to prevent secondary infections and cross infections after the sterilization process. For effective sterilization processes, TIVEK having selective permeability is generally used on one side of a film of the pouch. Meanwhile, on the other side, a transparent film (e.g., a PE, PET, or PE-PET film) is used so that an internal article to be sterilized can be seen. Here, the selective permeability allows permeation of the sterilant through the film to perform the sterilization process, and sterility after the sterilization process may be maintained because bacteria are not permeated. However, since the sterilant is partially absorbed into the TIVEK film during the sterilization process, there is a problem that the sterilant is lost as a result and efficiency of the sterilization process is inferior. Therefore, a sufficient purification process is required after the sterilization process to prevent the sterilant from being absorbed into the film of the packaging pouch or to prevent the sterilant remaining on a surface of the film of the packaging pouch from being exposed to a user.

After the sterilization process, the sterilization process removes a sterilant remaining on the inner surface of a sterilization chamber and an inside of the packaging pouch using the conventional TIVEK, the film, and the surface of the film to ensure user safety by performing processes such as vacuum formation, aeration, and plasma discharge in an additional sterilization chamber. However, such an indirect purification process is ineffective in removing a sterilant remaining on an article to be sterilized, and a long time purification process is required to ensure user safety.

Therefore, the inventors of the present invention propose a sterilized packaging container, which includes a sterilant injection block that allows direct sterilant injection into the packaging container without using a film having selective permeability, in which an appropriate amount of sterilant for the packaging container is stored in the sterilant injection block.

DETAILED DESCRIPTION OF THE INVENTION

Technical Problem

The present invention is directed to a sterilization apparatus for suppressing the use of an unnecessary large amount of sterilant by minimizing a sterilization space and for sterilizing an object to be treated which has been loaded into a vacuum packaging pouch which is vacuum packed or a vacuum chamber.

The present invention is directed to a sterilant injection block mounted in a vacuum chamber and containing a sterilant.

The present invention is directed to a sterilization apparatus capable of extracting a sterilant from a sterilant injection block containing a sterilant, vaporizing and activating the sterilant, and injecting the sterilant into a vacuum chamber to perform effective sterilization.

The present invention is directed to a sterilization apparatus capable of loading a sterilant injection block including a sterilant or a vacuum packaging pouch having the sterilant injection block into a vacuum chamber, and sterilizing an inside of the vacuum chamber or an inside of the vacuum packaging pouch according to conditions.

The present invention is directed to a sterilant injection block for directly injecting a sterilant into the inside of a packaging container.

The present invention is directed to a vacuum packaging container for directly injecting a sterilant into a vacuum chamber.

The present invention is directed to a sterilant injection block for storing an appropriate amount of sterilant according to the volume of a vacuum packaging container or a vacuum chamber and for supplying the sterilant to a sterilizer.

The present invention is not limited to the above objectives, but other objectives not described herein may be clearly understood by those of ordinary skill in the art from descriptions below.

Technical Solution

According to an example embodiment, a sterilization apparatus comprises a sterilant injection block comprising a sterilant container containing a sterilant and being sealed and sterilant container stopper of an elastic material blocking the sterilant container; a vacuum chamber having a door and containing the sterilant injection block; a main needle disposed outside the vacuum chamber and injecting a sterilant into the vacuum chamber through the sterilant injection block; and a vacuum pump evacuating the vacuum chamber.

According to an example embodiment, the sterilant injection block comprises: a sterilant injection path; and a sterilant injection path stopper of an elastic material blocking the sterilant injection path, wherein the main needle is configure to pierce the sterilant injection path stopper.

According to an example embodiment, the sterilant injection block forms a portion of a vacuum packaging pouch.

According to an example embodiment, the sterilization apparatus further comprises an auxiliary needle disposed outside the vacuum chamber and piercing the sterilant container stopper to extract the sterilant.

According to an example embodiment, the sterilization apparatus further comprises a vaporizer disposed outside the vacuum chamber and vaporizing the sterilant extracted through the auxiliary needle, wherein the vaporized sterilant is supplied to the vacuum chamber through the sterilant injection path of the sterilant injection block through the main needle.

According to an example embodiment, the sterilization apparatus further comprises a heating block disposed within the vacuum chamber and contacting the sterilant injection block to heat the sterilant injection block.

According to an example embodiment, a lower surface of the vacuum chamber supports the sterilant injection block and provides an opening for a needle through which the main needle can pass.

According to an example embodiment, the sterilization apparatus further comprises a main needle transfer portion configured to vertically transfer the main needle.

According to an example embodiment, the sterilant injection block comprises: an upper strip and a lower strip having opposite ends bent to contact each other and central portions extending parallel to each other; a barrier wall between the upper strip and the lower strip; a sterilant injection path formed through the upper strip; a sterilant injection path stopper disposed on the upper strip to block the sterilant injection path; and an alignment strip extending laterally along a side of the upper strip and the lower strip to seal the side of the upper strip and the lower strip.

According to an example embodiment, the sterilant injection block further comprises: a sterilant container disposed to be spaced apart from the sterilant injection path and containing the sterilant and being sealed; and a sterilant container stopper of an elastic material disposed on the upper strip and blocking the sterilant container.

According to an example embodiment, the sterilant injection block further comprises: a first sterilant container disposed to be spaced apart from the sterilant injection path and containing the sterilant and being sealed; and a first sterilant container stopper of an elastic material disposed on the upper strip and blocking the sterilant container; a second sterilant container disposed at a lower portion of the first sterilant container stopper and containing the sterilant and being sealed; and a second sterilant container stopper between the first sterilant container and the second sterilant container.

According to an example embodiment, the sterilant injection block comprises: a disk-shaped sealing plate; an upper protrusion protruding from an upper surface of the sealing plate; a lower protrusion protruding from a lower surface of the sealing plate; a sterilant injection path passing through the upper protrusion and the sealing plate and opened to a side surface of the lower protrusion; and a sterilant injection path stopper blocking the sterilant injection path on an upper surface of the upper protrusion.

According to an example embodiment, the sterilant injection block further comprises: a sterilant container disposed in the upper protrusion and containing the sterilant and being sealed; and a sterilant container stopper of an elastic material disposed in the upper protrusion and blocking the sterilant container.

According to an example embodiment, the sterilant injection block comprises: a body portion comprising a base plate and a protrusion protruding from the base plate; a sterilant injection block cover inserted into a depression recessed in an upper surface of the protrusion; and a sterilant injection path stopper between the sterilant injection block cover and a lower surface of the depression and made of an elastic material, wherein the body portion comprises a first through hole passing through the depression, the sterilant injection block cover comprises a second through hole aligned with the first through hole, and the first through hole and the second through hole provide the sterilant injection path.

According to an example embodiment, the sterilant injection block further comprises: a sterilant container disposed on the lower surface of the depression and containing the sterilant; and a sterilant container stopper of an elastic material between the sterilant container and the sterilant injection block cover and blocking the sterilant container, wherein the sterilant injection block cover comprises a third through hole aligned with the sterilant container, and the sterilant container stopper and the sterilant injection path stopper are integrated.

According to an example embodiment, the sterilant injection block comprises: an upper strip and a lower strip having opposite ends bent to contact each other and central portions extending parallel to each other; a barrier wall between the upper strip and the lower strip; a sterilant injection path formed through the upper strip and opened at the side; a sterilant injection path stopper of an elastic material disposed on the upper strip to block the sterilant injection path; and an alignment strip extending laterally along a side of the upper strip and the lower strip to seal the side of the upper strip and the lower strip.

According to an example embodiment, the sterilant injection block further comprises: a sterilant container disposed to be spaced apart from the sterilant injection path and containing the sterilant and being sealed; and a sterilant container stopper of an elastic material disposed on the upper strip and blocking the sterilant container.

According to an example embodiment, the sterilant injection block has a bar code or a QR code.

According to an example embodiment, a sterilization method comprises: an operation in which a sterilant injection block for containing a sterilant and providing a sterilant injection path for injecting the sterilant or a vacuum packaging pouch having the sterilant injection block is mounted inside a vacuum chamber; and an operation in which the vacuum chamber is operated in a chamber mode in which the vacuum chamber is used as a sterilization container when only the sterilant injection block is mounted and the vacuum packaging pouch is operated in a pouch mode in which the vacuum packaging pouch is used as a sterilization container when the vacuum packaging pouch is mounted.

According to an example embodiment, the chamber mode comprises: evacuating the vacuum chamber; lifting an auxiliary needle to extract a sterilant from the sterilant injection block; lifting a main needle; vaporizing the extracted sterilant and injecting the vaporized sterilant into the vacuum chamber through the main needle; lowering the auxiliary needle; lowering the main needle; evacuating the sterilant from the vacuum chamber; and venting the vacuum chamber.

According to an example embodiment, the pouch mode comprises: lifting a main needle; evacuating the vacuum chamber and evacuating the vacuum packaging pouch through the main needle; lifting an auxiliary needle to extract a sterilant from the sterilant injection block; vaporizing the extracted sterilant and injecting the sterilant into the vacuum packaging pouch through the main needle; lowering the auxiliary needle; evacuating the sterilant from the vacuum packaging pouch through the main needle; venting the vacuum chamber and venting the vacuum packaging pouch using the main needle; and lowering the main needle.

According to an example embodiment, the sterilant is hydrogen peroxide.

According to an example embodiment, the sterilant injection block comprises a bar code or a QR code, and performs a sterilization process according to information recorded in the bar code or the QR code.

According to an example embodiment, a sterilization method comprises: mounting a sterilant injection block for containing a sterilant and providing a sterilant injection path injecting the sterilant inside a vacuum chamber; vacuum evacuating the interior of the vacuum chamber; extracting the sterilant from the sterilant injection block and injecting the sterilant into the vacuum chamber through the sterilant injection block to sterilize an object to be treated disposed in the vacuum chamber; and evacuating the sterilant from the vacuum chamber.

According to an example embodiment, the sterilization method further comprises: heating the sterilant injection block in the vacuum chamber; and venting the vacuum chamber to an atmospheric pressure after evacuating the sterilant.

According to an example embodiment, the sterilant is hydrogen peroxide, and the sterilant is vaporized and injected into the vacuum chamber through the sterilant injection block.

According to an example embodiment, the sterilant injection block comprises a bar code or a QR code, and performs a sterilization process according to information recorded in the bar code or the QR code.

According to an example embodiment, a sterilization method comprises: mounting a vacuum packaging pouch having a sterilant injection block for containing a sterilant and providing a sterilant injection path for injecting the sterilant, inside a vacuum chamber; vacuum evacuating the interior of the vacuum chamber and the vacuum packaging pouch; extracting the sterilant from the sterilant injection block and injecting the sterilant into the vacuum packaging pouch through the sterilant injection block to sterilize an object to be treated disposed in the vacuum packaging pouch; and evacuating the sterilant from the vacuum packaging pouch.

According to an example embodiment, the sterilization method further comprises: heating the sterilant injection block in the vacuum chamber; and venting the vacuum chamber to an atmospheric pressure after evacuating the sterilant.

According to an example embodiment, the sterilant is hydrogen peroxide, and the sterilant is vaporized and injected into the vacuum packaging pouch through the sterilant injection block.

According to an example embodiment, the sterilant injection block comprises a bar code or a QR code, and performs a sterilization process according to information recorded in the bar code or the QR code.

According to an example embodiment, a sterilant injection block comprises: an upper strip and a lower strip having opposite ends bent to contact each other and central portions extending parallel to each other; a barrier wall between the upper strip and the lower strip; a sterilant injection path formed through the upper strip; a sterilant injection path stopper disposed on the upper strip to block the sterilant injection path; and an alignment strip extending laterally along a side of the upper strip and the lower strip to seal the side of the upper strip and the lower strip.

According to an example embodiment, the sterilant injection block further comprises: a sterilant container disposed to be spaced apart from the sterilant injection path and containing the sterilant and being sealed; and a sterilant container stopper of an elastic material disposed on the upper strip and blocking the sterilant container.

According to an example embodiment, the sterilant injection block further comprises: a first sterilant container disposed to be spaced apart from the sterilant injection path and containing the sterilant and being sealed; a first sterilant container stopper of an elastic material disposed on the upper strip and blocking the sterilant container; a second sterilant container disposed at a lower portion of the first sterilant container stopper and containing the sterilant and being sealed; and a second sterilant container stopper between the first sterilant container and the second sterilant container.

According to an example embodiment, the sterilant injection block further comprises a bar code or a QR code.

According to an example embodiment, a sterilant injection block comprises: a disk-shaped sealing plate; an upper protrusion protruding from an upper surface of the sealing plate; a lower protrusion protruding from a lower surface of the sealing plate; a sterilant injection path passing through the upper protrusion and the sealing plate and opened to a side surface of the lower protrusion; and a sterilant injection path stopper blocking the sterilant injection path on an upper surface of the upper protrusion.

According to an example embodiment, the sterilant injection block further comprises: a sterilant container disposed in the upper protrusion and containing the sterilant and being sealed; and a sterilant container stopper of an elastic material disposed in the upper protrusion and blocking the sterilant container, wherein the sterilant container stopper and the sterilant injection path stopper are integrated.

According to an example embodiment, the sterilant injection block further comprises a bar code or a QR code.

According to an example embodiment, a sterilant injection block of claim comprises: a body portion comprising a base plate and a protrusion protruding from the base plate; a sterilant injection block cover inserted into a depression recessed in an upper surface of the protrusion; and a sterilant injection path stopper between the sterilant injection block cover and a lower surface of the depression and made of an elastic material, wherein the body portion comprises a first through hole passing through the depression, the sterilant injection block cover comprises a second through hole aligned with the first through hole, and the first through hole and the second through hole provide a sterilant injection path.

According to an example embodiment, the sterilant injection block further comprises: a sterilant container disposed on a lower surface of the depression and containing the sterilant; and a sterilant container stopper of an elastic material between the sterilant container and the sterilant injection block cover and blocking the sterilant container, wherein the sterilant injection block cover comprises a third through hole aligned with the sterilant container, and the sterilant container stopper and the sterilant injection path stopper are integrated.

According to an example embodiment, the sterilant injection block further comprises a bar code or a QR code.

According to an example embodiment, a sterilant injection block comprises: an upper strip and a lower strip having opposite ends bent to contact each other and central portions extending parallel to each other; a barrier wall between the upper strip and the lower strip; a sterilant injection path formed through the upper strip and opened at the side; a sterilant injection path stopper of an elastic material disposed on the upper strip to block the sterilant injection path; and an alignment strip extending laterally along a side of the upper strip and the lower strip to seal the side of the upper strip and the lower strip.

According to an example embodiment, the sterilant injection block further comprising: a sterilant container disposed to be spaced apart from the sterilant injection path and containing the sterilant and being sealed; and a sterilant container stopper of an elastic material disposed on the upper strip and blocking the sterilant container.

According to an example embodiment, the sterilant injection block further comprises a bar code or a QR code.

Advantageous Effects of the Invention

A sterilization apparatus according to an embodiment of the present invention may selectively supply a sterilant to the inside of a vacuum packaging pouch or a vacuum chamber to greatly increase the efficiency of use of the sterilant, and may ensure user safety because there is no sterilant remaining on an outer surface of the packaging container after a sterilization process.

A vacuum packaging pouch according to an embodiment of the present invention includes an appropriate amount of sterilant for a sterilization process. A sterilizer does not need a sterilant supply in a fixed amount, and a user does not need to supply a sterilant repeatedly to the sterilizer, thereby improving user convenience. In addition, the sterilizer recognizes sterilizer capacity before the sterilization process and information about the type and date of manufacture of a packaging container by using code such as a bar code or a QR code printed on the packaging container or a sterilant injection block. Accordingly, after confirming setting of the sterilization process, confirmation of use of the sterilant, and effectiveness of the sterilant, the sterilization process may be performed to ensure sterilization reliability. In addition, it is possible to track and manage an article to be sterilized (object to be treated), thereby improving the reliability of a medical service.

According to an embodiment of the present invention, sterilization efficiency may be improved by directly injecting a sterilant into a packaging pouch (vacuum packaging pouch) which may be sealed by using a non-permeable film, and a user safety problem which occurs when the sterilant is absorbed into a pouch film or remains on an outer surface of the pouch film may be solved.

According to an embodiment of the present invention, unlike a packaging pouch using a conventional semi-permeable film, the use of a non-permeable film for the packaging pouch enables vacuum sealing of the packaging pouch after a sterilization process, thereby greatly improving aseptic preservability.

According to an embodiment of the present invention, it is possible to effectively raise the temperature inside a pouch through a heating block and evacuate a sterilant remaining in the pouch after a hydrogen peroxide sterilization process, thereby ensuring efficiency of the sterilization process and user safety.

According to an embodiment of the present invention, a vacuum chamber is used to remove a pressure difference and to ensure the volume of a vacuum packaging pouch, and the vacuum packaging pouch performs a sterilization process in a small space, thereby reducing sterilant usage.

BRIEF DESCRIPTION OF THE DRAWINGS

FIG. 9A is a plan view of a vacuum packaging pouch used in the sterilization apparatus of FIG. 8.

BEST MODE OF THE INVENTION

Figure 1A:
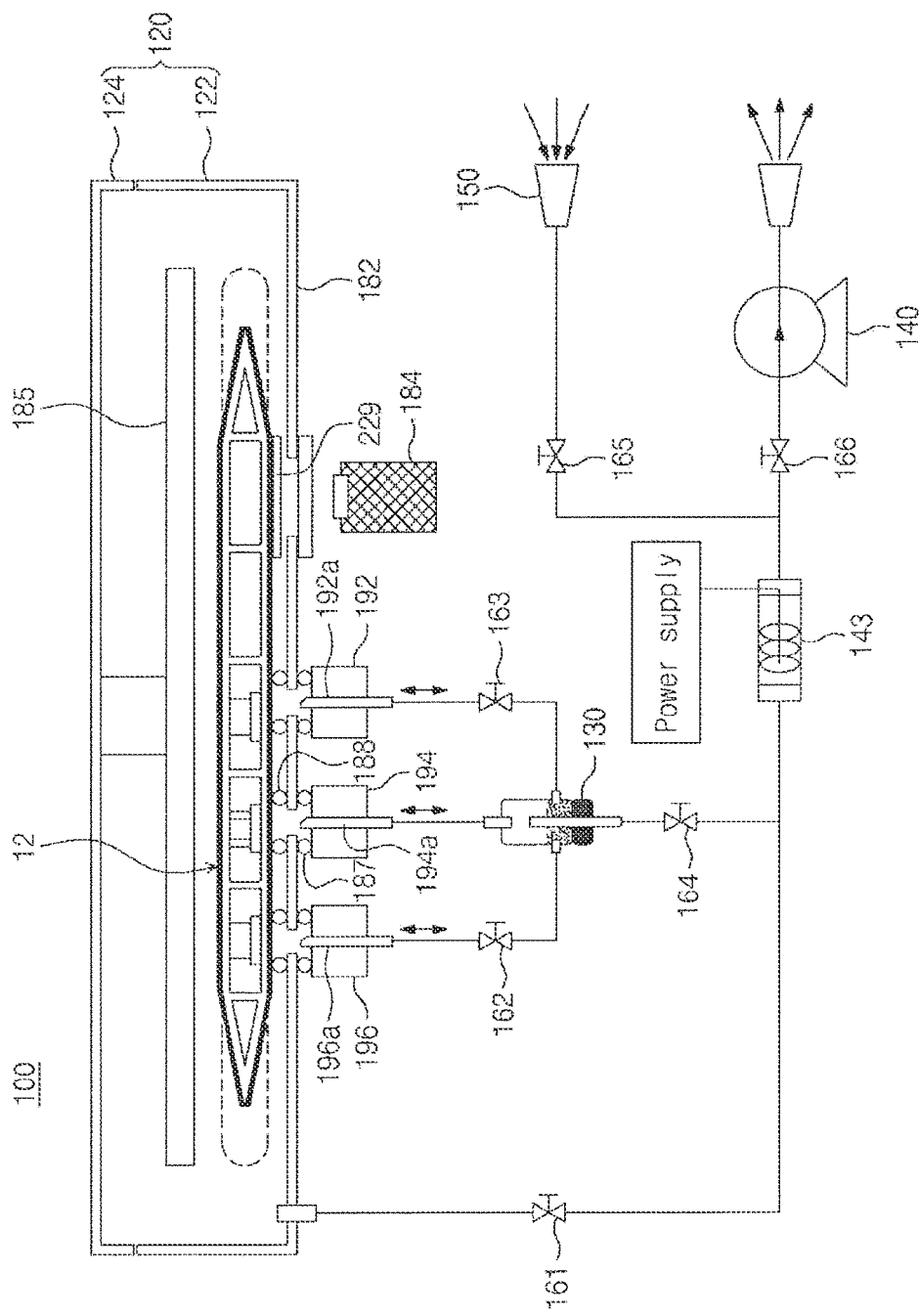
FIGS. 1A to 1C are conceptual diagrams of a sterilization apparatus according to an embodiment of the present invention.

Chemical sterilization using a sterilant typically places a packaging pouch inside a sterilization chamber, including a selective permeable film, such as TIVEK, through which the sterilant may permeate an object to be treated. When the sterilant is injected into the sterilization chamber, the sterilant permeates the packaging pouch to sterilize the object to be treated in the packaging pouch. Sterilization efficiency of the sterilization method is drastically reduced due to a separate packaging pouch. In addition, the packaging pouch requires an additional long period of purification to remove the sterilant adsorbed on the packaging pouch in the sterilization process. As the sterilant is injected into the sterilization chamber, a large amount of sterilant is used. The sterilant may cause environmental pollution. Further, the sterilant is usually subjected to an exhaust purification process before being exhausted to the outside. This exhaust purification process deteriorates the performance of a vacuum pump. Therefore, a new sterilization method using a small amount of sterilant is required.

According to an embodiment of the present invention, a vacuum packaging pouch is used instead of a sterilization chamber to carry out a sterilization process. After completion of the sterilization process, the vacuum packaging pouch may be immediately transmitted by a user or stored for a long time. When the sterilant is injected into the vacuum packaging pouch, the volume defined by the vacuum packaging pouch is significantly less than the volume of the conventional sterilization chamber. Therefore, the sterilant usage may be significantly reduced.

The vacuum packaging pouch may be evacuated in a vacuum state under an atmospheric pressure by a vacuum pump, and a sterilant may be injected into the vacuum packaging pouch. When the vacuum packaging pouch is in an atmospheric pressure environment, the vacuum packaging pouch shrinks due to a pressure difference between the inside and the outside, and it is difficult to ensure a diffusion space of the sterilant. In order to provide the diffusion space of the sterilant, the vacuum packaging pouch may be arranged in a vacuum chamber maintained at a pressure lower than a pressure of the vacuum packaging pouch. Accordingly, the vacuum packaging pouch expands due to a low external pressure, thereby securing the diffusion space of the sterilant. Thus, the secured space may provide a path through which the sterilant can diffuse, thereby stably sterilizing an object to be treated such as a lumen. The vacuum chamber is for controlling the external pressure of the vacuum packaging pouch, and the sterilant is not exposed to an inner wall of the vacuum chamber. Accordingly, the air exhausted from the vacuum chamber may be separately purified and may not be exhausted. Therefore, only the sterilant injected into the vacuum packaging pouch may be selectively purified and exhausted.

The sterilization apparatus according to an embodiment of the present invention may be set to selectively sterilize an object to be treated that is packaged in a packaging pouch including a selective permeable film, such as a conventional TIVEK. In this case, a sterilant injection block for containing a sterilizer may be used instead of the vacuum packaging pouch. Accordingly, the sterilization apparatus of the present invention may perform sterilization by selecting any one of a conventional sterilization method having a packaging pouch including a selective permeable film and a sterilization method having a vacuum packaging pouch.

According to an embodiment of the present invention, when the vacuum packaging pouch is in a vacuum state, heat transfer due to convection is difficult. Therefore, a heating block may be used to heat the object to be treated to a specific temperature required for an optimal sterilization process.

According to an embodiment of the present invention, a sterilant is directly injected into a vacuum packaging pouch capable of vacuum sealing using an impermeable film, and sterilization efficiency is improved by a limited diffusion space of the sterilant. Also, a user safety problem that occurs when the sterilant is absorbed by the vacuum packaging pouch or remains on an outer surface of the vacuum packaging pouch may be solved. In addition, the vacuum packaging pouch may be vacuum packed to provide long-term storage in a sterilized state. The vacuum packaging pouch may maintain the sterilized state even in a contaminated environment, a high temperature environment, and a high humidity environment. A sterilant inlet (or a sterilant injection block) of the vacuum packaging pouch may be sealed by elasticity using an elastic body such as silicone rubber and a needle.

According to an embodiment of the present invention, the volume of a vacuum packaging pouch is ensured by using a vacuum container outside the vacuum packaging pouch without forming a flow path such as an embossing pattern to provide a diffusion space of a sterilant.

According to an embodiment of the present invention, it is necessary to ensure the volume of a vacuum packaging pouch for effective diffusion of a sterilant inside the vacuum packaging pouch and supply of the sterilant to an article to be sterilized after direct sterilant supply to the vacuum packaging pouch. For this purpose, an effective sterilization process is enabled by using a vacuum container outside the vacuum packaging pouch.

According to an embodiment of the present invention, a vacuum packaging pouch is sealed using a PE (polyethylene) film in a state in which an object to be treated is contained, and vacuum treatment of the vacuum packaging pouch and direct sterilant supply are possible through a sterilant injection block mounted in the vacuum packaging pouch.

According to an embodiment of the present invention, a vacuum packaging pouch may include a sterilant injection block and a sterilant container capable of containing a sterilant in the sterilant injection block. The sterilant may be extracted from the sterilant container and injected into the vacuum packaging pouch. Accordingly, a separate sterilant cartridge may be removed.

According to an embodiment of the present invention, a sterilant injection block may be mounted on a vacuum packaging pouch to directly inject a sterilant from a sterilizer into the vacuum packaging container to provide effective sterilization.

According to an embodiment of the present invention, by storing a sterilant in a sterilant injection block, leakage of the sterilant during a process of storing an appropriate amount of sterilant for the volume of a packaging container and extracting the sterilant contained in the sterilant injection block by using a structure such as silicon does not occur, and the reliability of user safety and a sterilization process may be ensured. In addition, it is possible to perform a reliable sterilization process by transmitting information about the amount of sterilant injected by using code such as a bar code or a QR code printed on a packaging pouch or a sterilant injection block, the type of packaging container, date of manufacture, etc. to the sterilizer. Furthermore, warning information may be displayed when a used vacuum packaging pouch is loaded again into a sterilization chamber by using information such as a bar code. Also, the information such as a bar code may be used to set a process mode according to this information.

Furthermore, according to a modified embodiment of the present invention, the vacuum chamber is also used as a sterilization chamber to treat a large-sized object to be treated which is not inserted into the vacuum packaging pouch.

Hereinafter, embodiments of the present invention will be described in detail with reference to the accompanying drawings. Advantages and features of the present invention, and implementation methods thereof will be clarified through following embodiments described with reference to the accompanying drawings. The present invention may, however, be embodied in many different forms and should not be construed as limited to the embodiments set forth herein. Rather, these embodiments are provided so that this disclosure will be thorough and complete, and will fully convey the concept of the present invention to one of ordinary skill in the art, and the present invention is only defined by the scope of claims.

Like reference numerals refer to like elements throughout. Accordingly, although the same reference numerals or like reference numerals are not mentioned or described in the drawings, they may be described with reference to other drawings. Further, even if the reference numerals are not shown, they may be described with reference to other drawings.

Figure 1B:
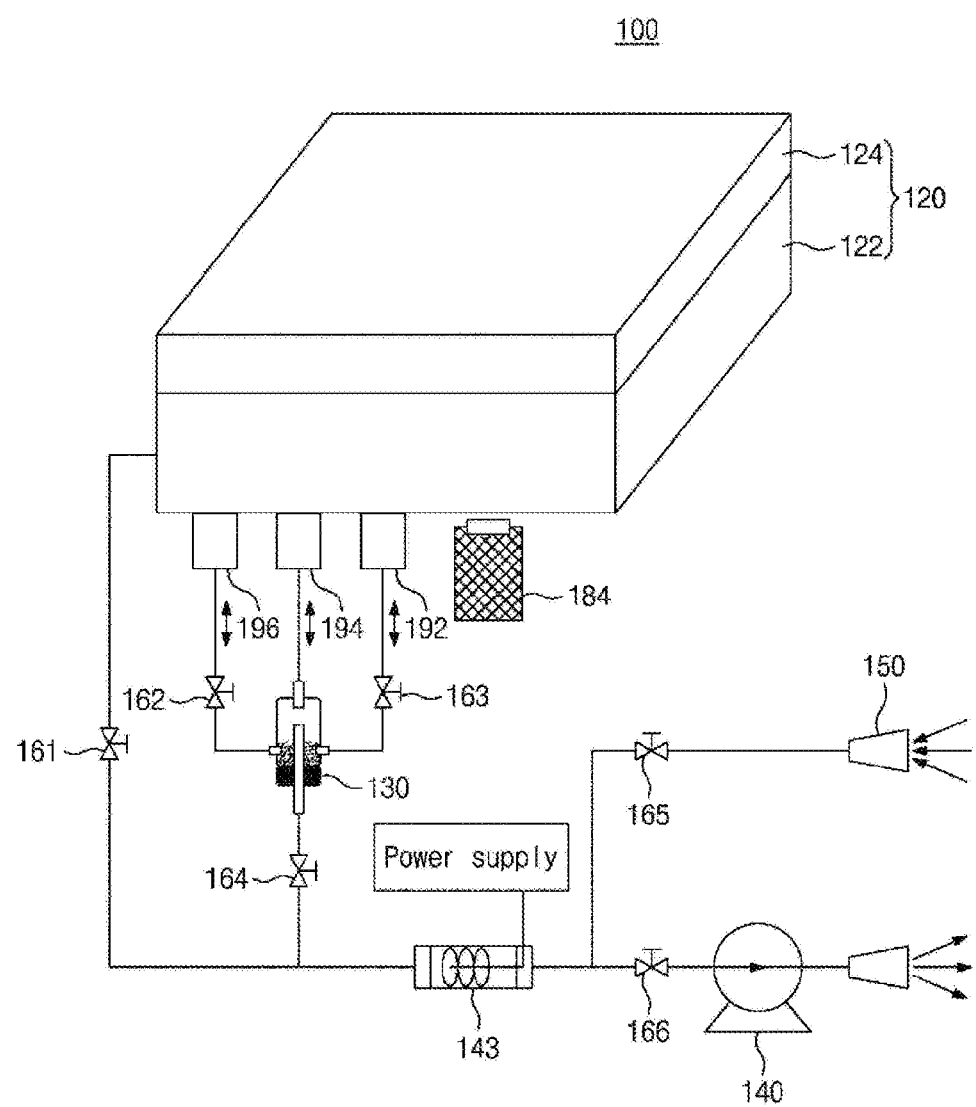
Figure 1C:
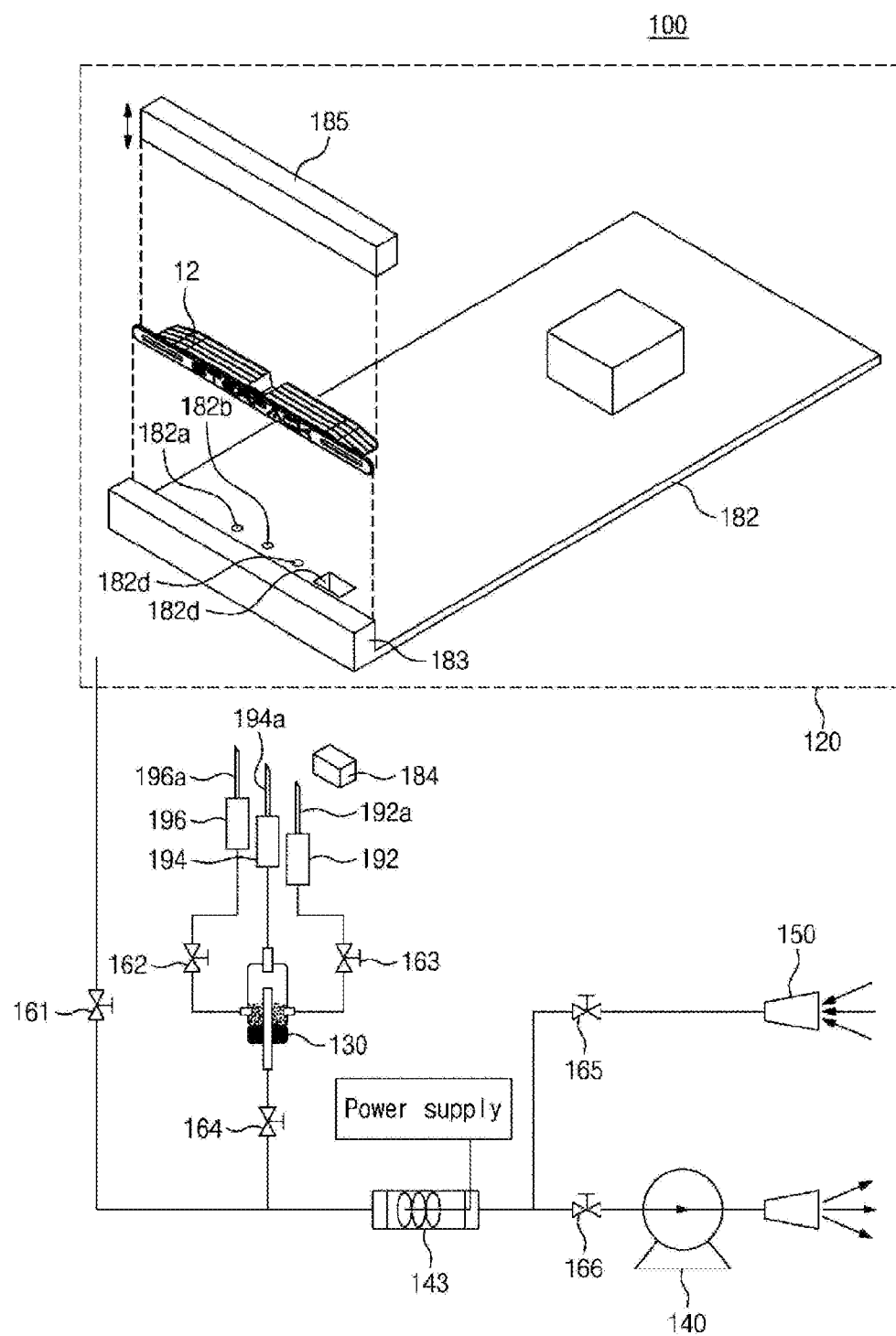

FIGS. 1A to 1C are conceptual diagrams of a sterilization apparatus according to an embodiment of the present invention.

Figure 2A:
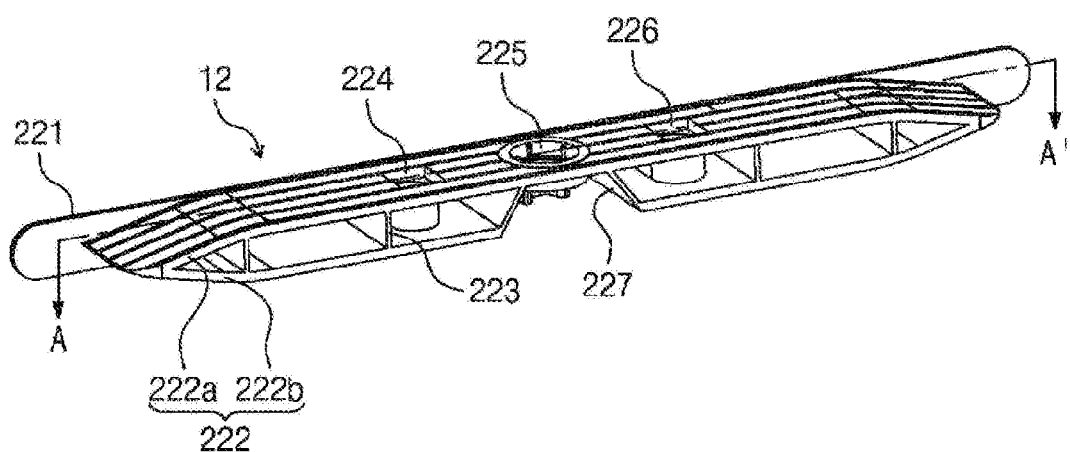
FIG. 2A is a perspective view of a sterilant injection block of the sterilization apparatus of FIG. 1A.

FIG. 2A is a perspective view of a sterilant injection block of the sterilization apparatus of FIG. 1A.

Figure 2B:
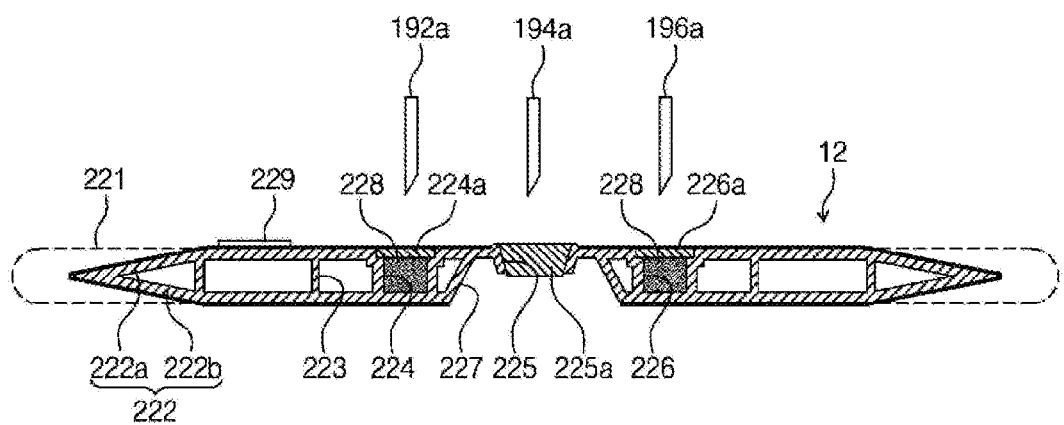
FIG. 2B is a cross-sectional view of the sterilant injection block of FIG. 2A.

FIG. 2B is a cross-sectional view of the sterilant injection block taken along a line A-A' of FIG. 2A.

Referring to FIGS. 1A to 1C and FIGS. 2A and 2B, a sterilization apparatus 100 includes: a sterilant injection block 12; a vacuum chamber 120 having a door 124 and containing the sterilant injection block 12; a main needle 196a disposed outside the vacuum chamber 120 and injecting a sterilant into the vacuum chamber 120 through the sterilant injection block 12; and a vacuum pump 140 for evacuating the vacuum chamber 120. The sterilant injection block 12 includes: sterilant containers 224 and 226 for containing the sterilant and being sealed; and sterilant container stoppers 224a and 226a of an elastic material blocking the sterilant containers.

The sterilization apparatus 100 may operate in a chamber mode in which the vacuum chamber is used as a chamber to which the sterilant is supplied and a pouch mode in which a sterilant is supplied into a separate vacuum packaging pouch.

In the chamber mode, the sterilant injection block 12 may provide a path for containing the sterilant and injecting the sterilant into the vacuum chamber 120. An object to be treated is a medical device and may be disposed inside the vacuum chamber. The object to be treated may be contained in a packaging pouch containing a selective permeable film such as TIVEK™.

Meanwhile, in the pouch mode, the vacuum packaging pouch is provided with the sterilant injection block. An object to be treated is a medical device and may be disposed inside the vacuum packaging pouch. The inside of the vacuum packaging pouch is vacuum evacuated, and a sterilant is supplied into the vacuum packaging pouch. In the pouch mode, in order to provide a constant volume of the vacuum packaging pouch, the vacuum chamber is evacuated to provide an environment in which the vacuum packaging pouch can be expanded by a pressure difference.

Hereinafter, the chamber mode will be described.

The vacuum chamber 120 may include the door 124 and a chamber body 122. The door 124 may be a cover of the vacuum chamber 120. The door 124 may be coupled to the vacuum chamber 120 by a rotating unit such as a hinge.

The vacuum chamber 120 may have a space for containing the sterilant injection block 12 and a heating block 185 therein. The vacuum chamber 120 may have a rectangular parallelepiped shape and may be formed of metal.

The vacuum chamber 120 may be connected to the vacuum pump 140 through a connection pipe and a valve. The vacuum pump 140 may vacuum evacuate the vacuum chamber 120.

A filter 150 may suck in the air to remove fine dust and bacteria and provide the air to the vacuum chamber 120.

A vaporizer 130 may vaporize the sterilant and inject the sterilant into the vacuum chamber 120. When the sterilant is hydrogen peroxide, the vaporizer 130 may heat and vaporize the sterilant at a temperature of 50° C. to 110° C. and may inject the vaporized sterilant into the vacuum chamber 120. The vaporizer 130 may be disposed outside the vacuum chamber.

The heating block 185 may be disposed within the vacuum chamber 120 and may contact the sterilant injection block 12 to heat the sterilant injection block 12. The heating block 185 is heated from 50° C. to 110° C. and may heat some or all of the sterilant injection block 12. The heating block 185 may be mounted on the door 124 of the vacuum chamber 120 to be vertically movable.

When the vacuum chamber 120 is vacuum evacuated, heat transfer through the air is impossible. Therefore, the heating block 185 may be pressed to directly contact the sterilant injection block 12. The heating block 185 may be in the shape of a rod having a rectangular cross section. The inside of the heating block 185 may be heated by a heating wire. The heating block 185 may press and heat the sterilant injection block 12.

A lower surface 182 of a vacuum container may align and support the sterilant injection block 12. Furthermore, the lower surface 182 of the vacuum container is plate-shaped and may include a plurality of openings 182a, 182b, 182c, and 182d to allow access to the sterilant injection block 12. The lower surface 182 of the vacuum container may include an alignment portion 183 protruding for alignment of the sterilant injection block 12. The lower surface 182 of the vacuum container is formed of metal and may be heated so as to be maintained at a constant temperature. The lower surface 182 of the vacuum container may support the sterilant injection block and provide the opening 182b for a main needle through which the main needle 194a can pass.

A sealing unit 188 on the lower surface 182 of the vacuum container may be in close contact with the sterilant injection block 12 to perform sealing. The sealing unit 188 may be an O-ring.

The main needle 194a may be arranged to pass through the opening 182b for a main needle in a lower surface of the vacuum container. An end of the main needle 194a is obliquely processed like a typical needle, and an opening (not shown) may be formed in a side surface of the end of the main needle 194a. A fluid path may be provided through an opening of the main needle. The main needle 194a may provide a path for supplying a sterilant from the outside to the inside of the vacuum chamber 120. An inner diameter of the main needle 194a may be at least 0.5 mm or more. A length of the main needle may be a few centimeters or less and the inner diameter of the main needle may be 0.5 mm or more. A material of the main needle may be metal or a metal alloy.

The main needle transfer portion 194 may provide vertical linear motion to the main needle 194a and may be disposed outside the vacuum container 120.

The main needle transfer portion 194 includes an auxiliary sealing unit 187 which is in contact with the lower surface 182 of the vacuum container around the opening 182b for a main needle to perform sealing.

Auxiliary needles 196a and 192a may extract a sterilant sealed in the sterilant injection block 12. The auxiliary needles 196a and 192a may extract the liquid sterilant contained in the sterilant container of the sterilant injection block 12.

Auxiliary needle transfer portions 196 and 192 provide linear motion to the auxiliary needles 196a and 192a and may be disposed inside the vacuum container.

A sealing unit on the lower surface 182 of the vacuum container may contact an upper strip 222a to seal around the sterilant container stoppers 224a and 226a. The sealing unit may be an O-ring. The auxiliary needle transfer portions 192 and 196 include an auxiliary sealing unit which is in contact with the lower surface 182 of the vacuum container around the openings 182a and 182c for an auxiliary needle to perform sealing.

The sterilant injection block 12 may be made of polyethylene (PE). The sterilant injection block 12 includes sterilant containers 224 and 226 for containing the sterilant and being sealed; and sterilant container stoppers 224a and 226a of an elastic material blocking the sterilant containers 224 and 226. The sterilant injection block 12 may include a sterilant injection path 225; and a sterilant injection path stopper 225a of an elastic material blocking the sterilant injection path 225. The sterilant injection path stopper 225a may be made of an elastic material such as silicone rubber. The sterilant injection path stopper 225a may be fixed by fitting and/or an adhesive. Thus, even when the main needle 194a pierces the sterilant injection path stopper 225a and then retreats, the sterilant injection path stopper 225a may maintain a sufficiently sealed state.

The main needle 194a may pierce the sterilant injection path stopper 225a. A material of the sterilant injection path stopper 225a may be silicone rubber or an elastic polymer material. When the main needle 194a pierces the sterilant injection path stopper 225a, the sterilant injection path stopper 225a may maintain a sealed state by elasticity. When fluid flows through the main needle 194a, the fluid may not leak through the sterilant injection path stopper 225a.

The sterilant injection block 12 may include sterilant containers 224 and 226 for containing a sterilant 228 and being sealed; and sterilant container stoppers 224a and 226a of an elastic material blocking the sterilant containers 224 and 226. The auxiliary needles 192a and 196a may respectively pierce the sterilant container stoppers 224a and 226a to extract the sterilant.

The vaporizer 130 vaporizes the sterilant 228 extracted through the auxiliary needle and the vaporized sterilant may be injected into the vacuum chamber 120 through the main needle 194a and the sterilant injection path 225.

The sterilant injection block 12 may include: an upper strip 222a and a lower strip 222b having opposite ends bent to contact each other and the central portions extending parallel to each other; a barrier wall 223 between the upper strip 222a and the lower strip 222b; a sterilant injection path 225 formed through the upper strip 222a; a sterilant injection path stopper 225a on the upper strip to block the sterilant injection path 225; and an alignment strip 221 extending laterally along one side of the upper strip 222a and the lower strip 222b to seal the one side of the upper strip and the lower strip.

The upper strip 222a may include lines protruding to be thermally compressed easily on an upper surface thereof. The lower strip 222b may include lines protruding to be thermally compressed easily on a lower surface of the lower strip. The lower strip 222b may be bent in a direction of the upper strip at a position facing the sterilant injection path 225 to provide an open space 227.

The sterilant injection block 12 may include: sterilant container stoppers 224a and 226a disposed to be spaced apart from the sterilant injection path and containing the sterilant and being sealed; and sterilant container stoppers 224a and 226a of an elastic material disposed on the upper strip and blocking the sterilant container.

A code adhesive tape 229 such as a bar code or a QR code to be printed may be attached to the sterilant injection block 12. It is possible to perform a reliable sterilization process by transmitting information about the amount of sterilant injected by using the code adhesive tape 229, the type of packaging container, date of manufacture, etc. to a sterilizer. A code reader 184 may extract the information of the code adhesive tape 229 through the opening 182d formed on the lower surface of the vacuum container.

The sterilization apparatus 100 may include a plurality of valves 161 to 166. The valve may be used to evacuate the vacuum chamber, inject a sterilant into the vacuum chamber, and vent the vacuum chamber to the atmosphere.

A sterilant decomposition unit 143 may be disposed at a front end of the vacuum pump 140 and may decompose or filter a sterilant discharged from the vacuum chamber. The sterilizer decomposition unit 143 may be a plasma source.

Figure 3:
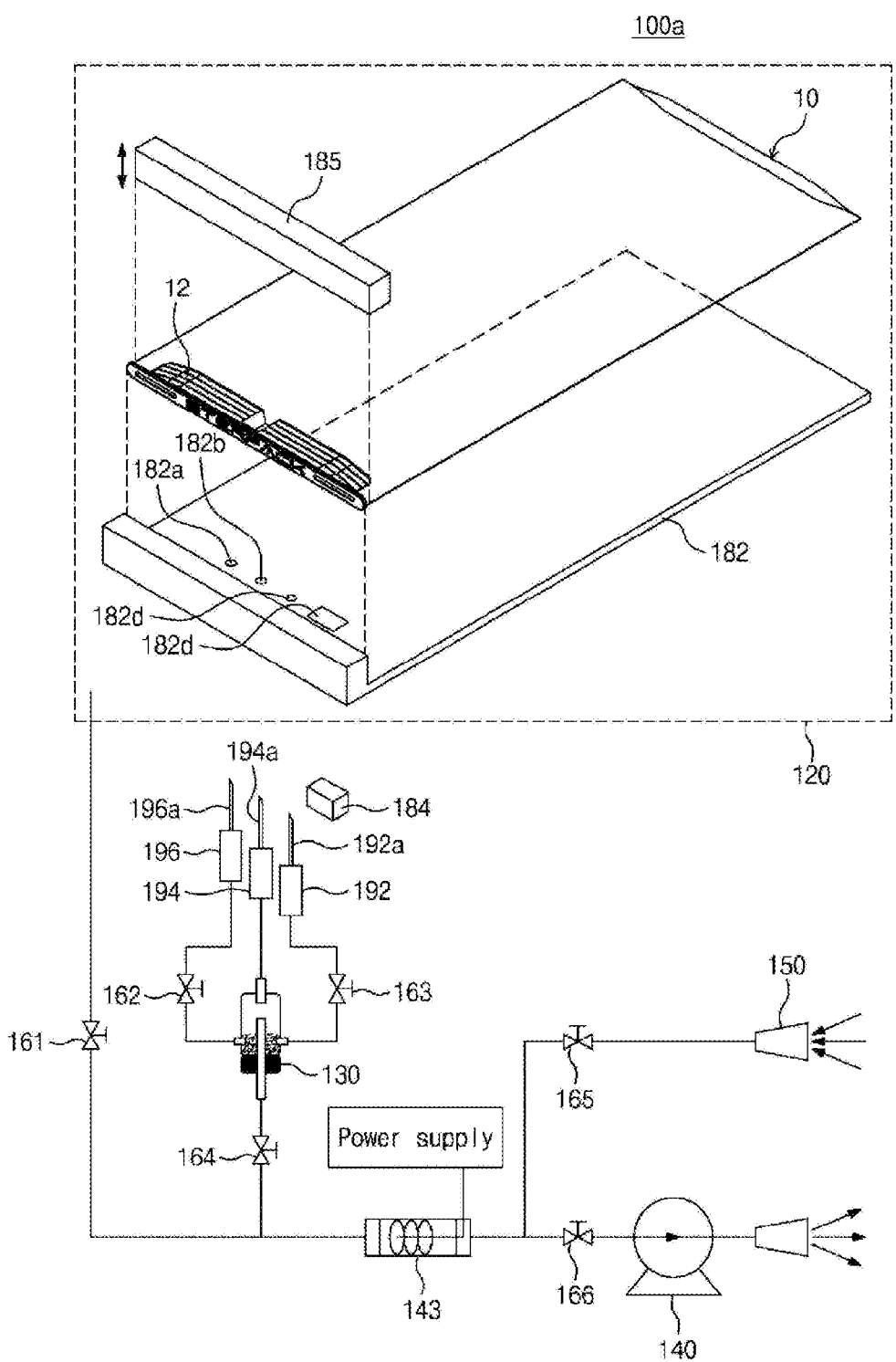
FIG. 3 is a conceptual diagram of a sterilization apparatus according to another embodiment of the present invention.

FIG. 3 is a conceptual diagram of a sterilization apparatus according to another embodiment of the present invention.

Figure 4A:
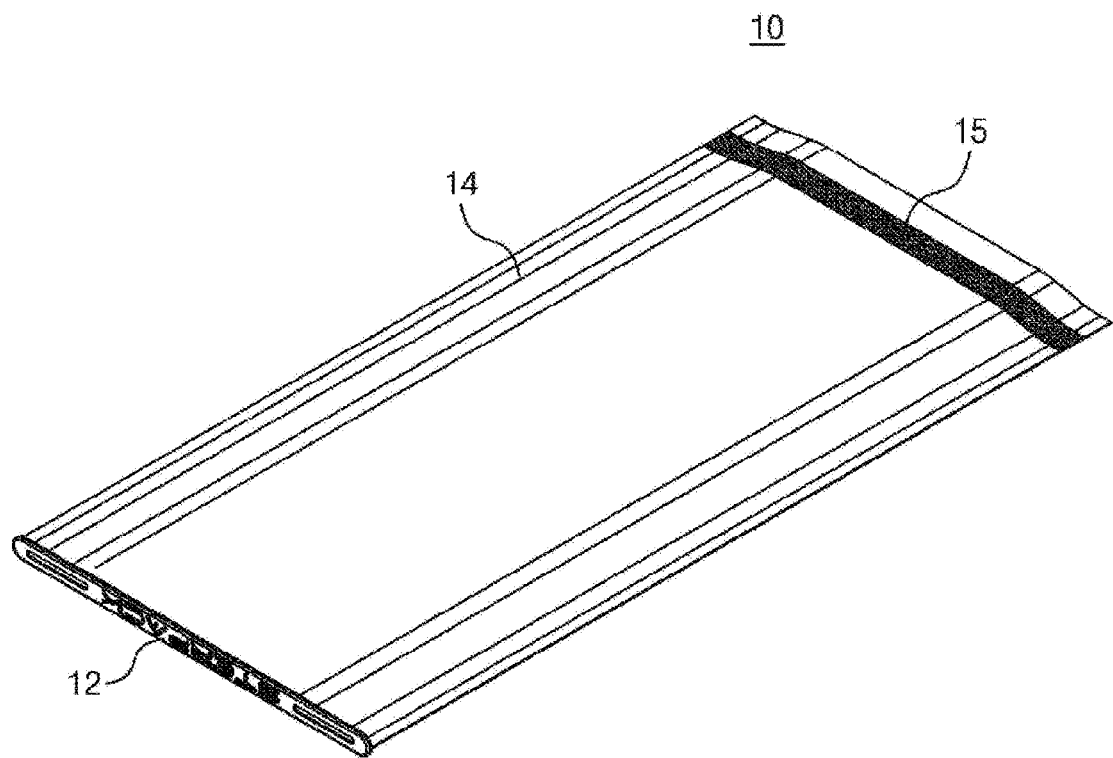
FIGS. 4A to 4C are a perspective view, a front view, and a rear view of a vacuum packaging pouch of the sterilization apparatus of FIG. 3.
Figure 4B:
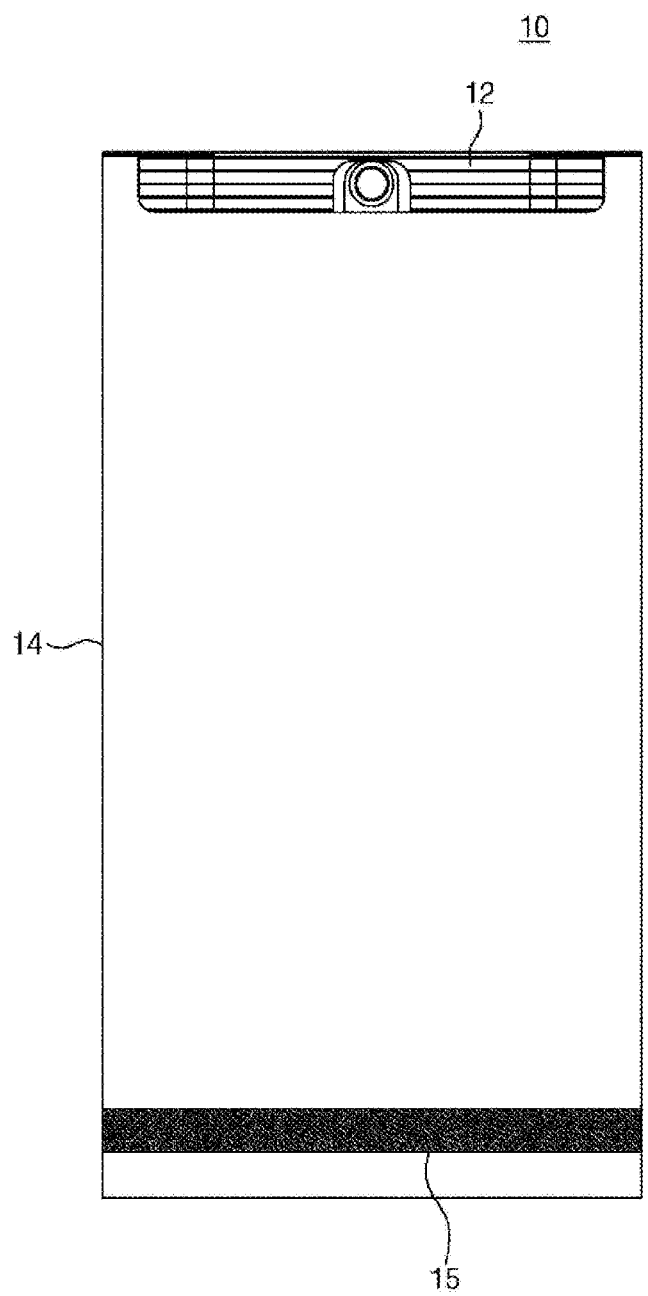
Figure 4C:
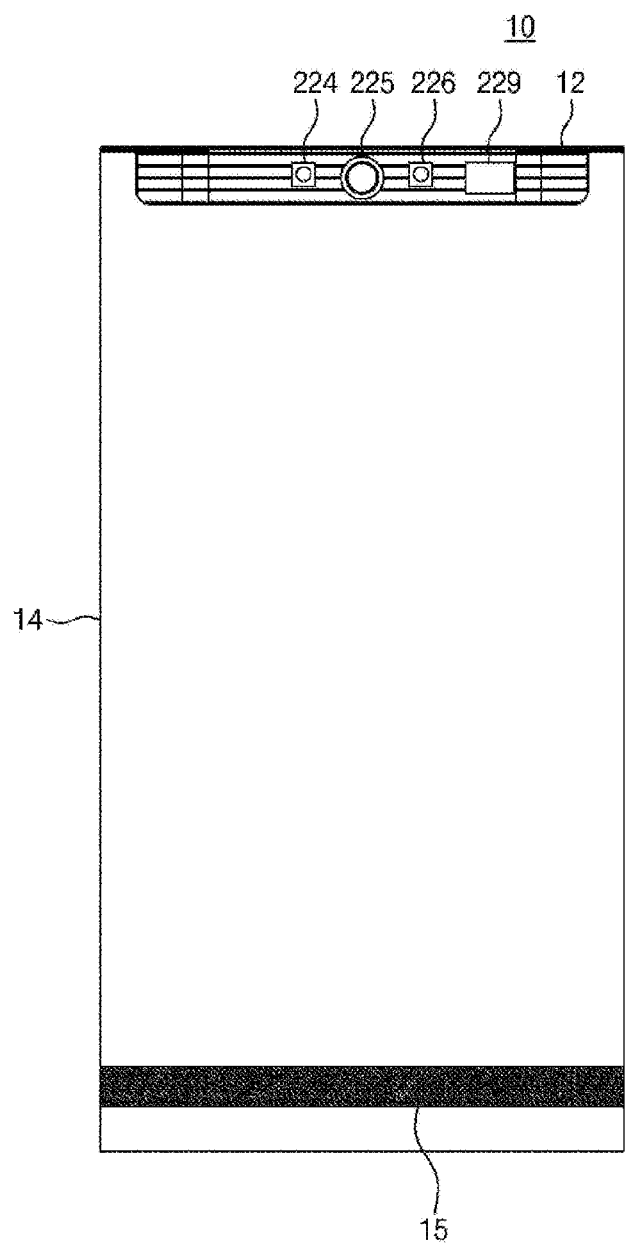

FIGS. 4A to 4C are a perspective view, a front view, and a rear view of a vacuum packaging pouch of the sterilization apparatus of FIG. 3.

Referring to FIG. 3, FIGS. 4A to 4C, and FIGS. 2A and 2B, a sterilization apparatus 100a includes: the vacuum packaging pouch 10 having the sterilant injection block 12 for containing an object to be treated (not shown) therein and being sealed to be in a vacuum state, and vacuum evacuating and injecting a sterilant from the outside; the vacuum chamber 120 having the door 124 and containing the vacuum packaging pouch 10; a main needle 194a for injecting a sterilant into the vacuum packaging pouch 10 and vacuum evacuating the vacuum packaging pouch 10; and the vacuum pump 140 for evacuating the vacuum packaging pouch 10 or the vacuum chamber 120. The sterilant injection block 12 provides a sealed space in combination with the vacuum packaging pouch 10. The object to be treated may be a medical device. The sterilant injection block 12 may form a portion of the vacuum packaging pouch 10. The vacuum packaging pouch 10 may be disposed under a vacuum environment to provide a constant volume due to a pressure difference even when the vacuum packaging pouch is in a vacuum state. The object to be treated may be contained in the vacuum packaging pouch 10 placed in a vacuum environment and sterilized.

Hereinafter, the pouch mode will be described.

The vacuum packaging pouch 10 is made of a nylon (NY) and/or PE material having sufficient flexibility and may be in the form of a bag sealed in a film form. The vacuum packaging pouch 10 may include a vacuum packaging bag 14 and the sterilant injection block 12 disposed at one end of the vacuum packaging bag. The other end of the vacuum packaging pouch 10 is initially opened, and after an object to be treated (e.g., a medical device) is inserted, the other end of the vacuum packaging pouch 10 may be sealed by a method such as thermocompression bonding so as to include a thermocompression bonding strip 15. The vacuum packaging pouch 10 may include the sterilant injection block 12 for vacuum evacuation and injecting a sterilant from the outside. A vacuum packaging bag 14 may be made of polyethylene. The vacuum packaging bag 14 may include a lower film and an upper film which provide an internal space by edge thermocompression bonding.

The vacuum chamber 120 may remove a pressure difference such that an internal pressure of the vacuum packaging pouch 10 is higher than an external pressure of the vacuum packaging pouch 10. That is, the vacuum chamber 120 may provide an environment in which the vacuum packaging pouch 10 may expand or an environment in which a certain internal volume may be ensured.

The main needle 194a may be used to inject a sterilant into the vacuum packaging pouch 10 and to evacuate the vacuum packaging pouch 10. Also, the main needle 194a may be used to exhaust the sterilant provided inside the vacuum packaging pouch 10.

In a case of the pouch mode, an object to be treated is contained in the vacuum packaging pouch. In addition, a sterilant is provided only inside the vacuum packaging pouch 10. In order to provide a volume for the sterilant to diffuse, the vacuum chamber 120 may be set to provide a pressure equal to or less than the internal pressure of the vacuum packaging pouch 10.

Figure 5:
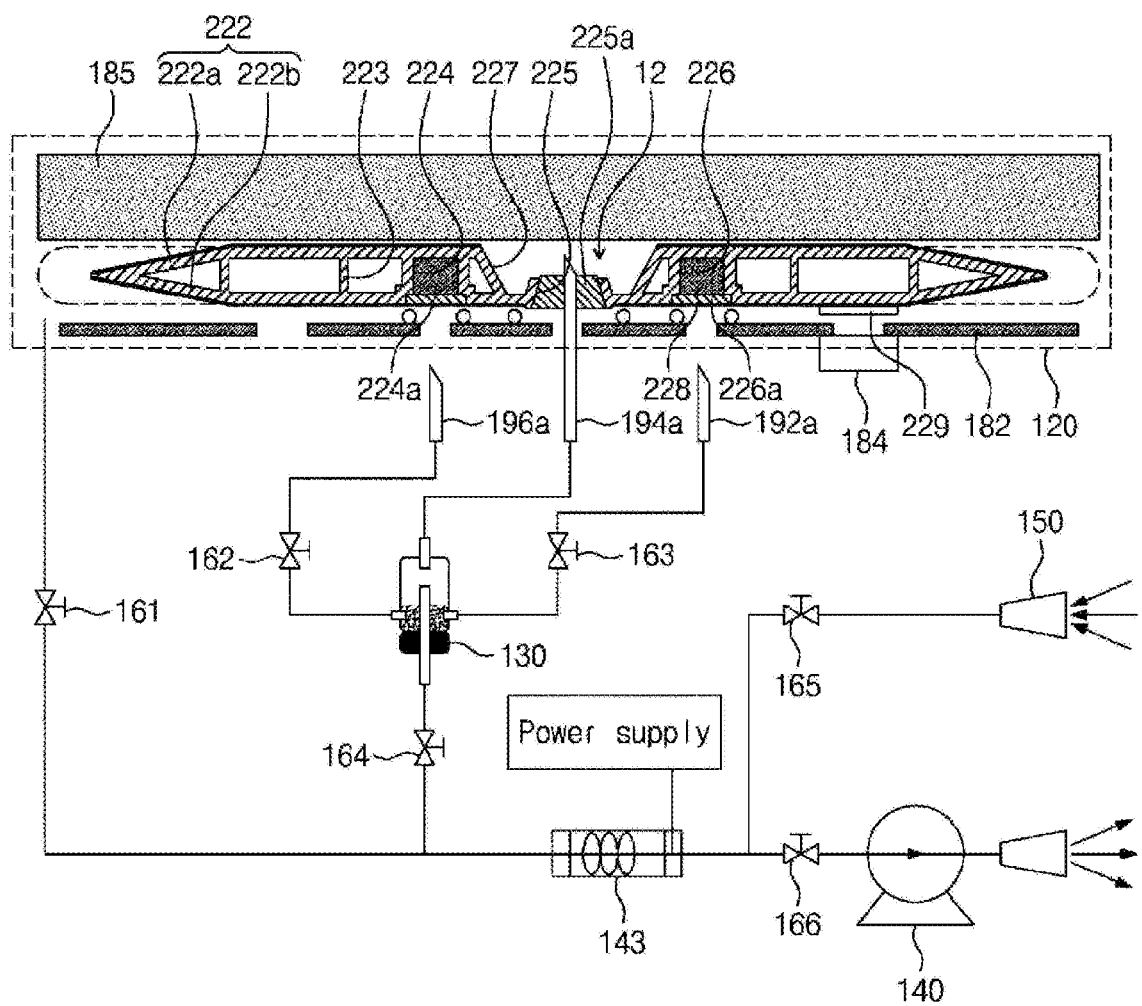
FIG. 5 is a conceptual diagram illustrating a sterilization method according to an embodiment of the present invention.

FIG. 5 is a conceptual diagram illustrating a sterilization method according to an embodiment of the present invention.

Figure 6:
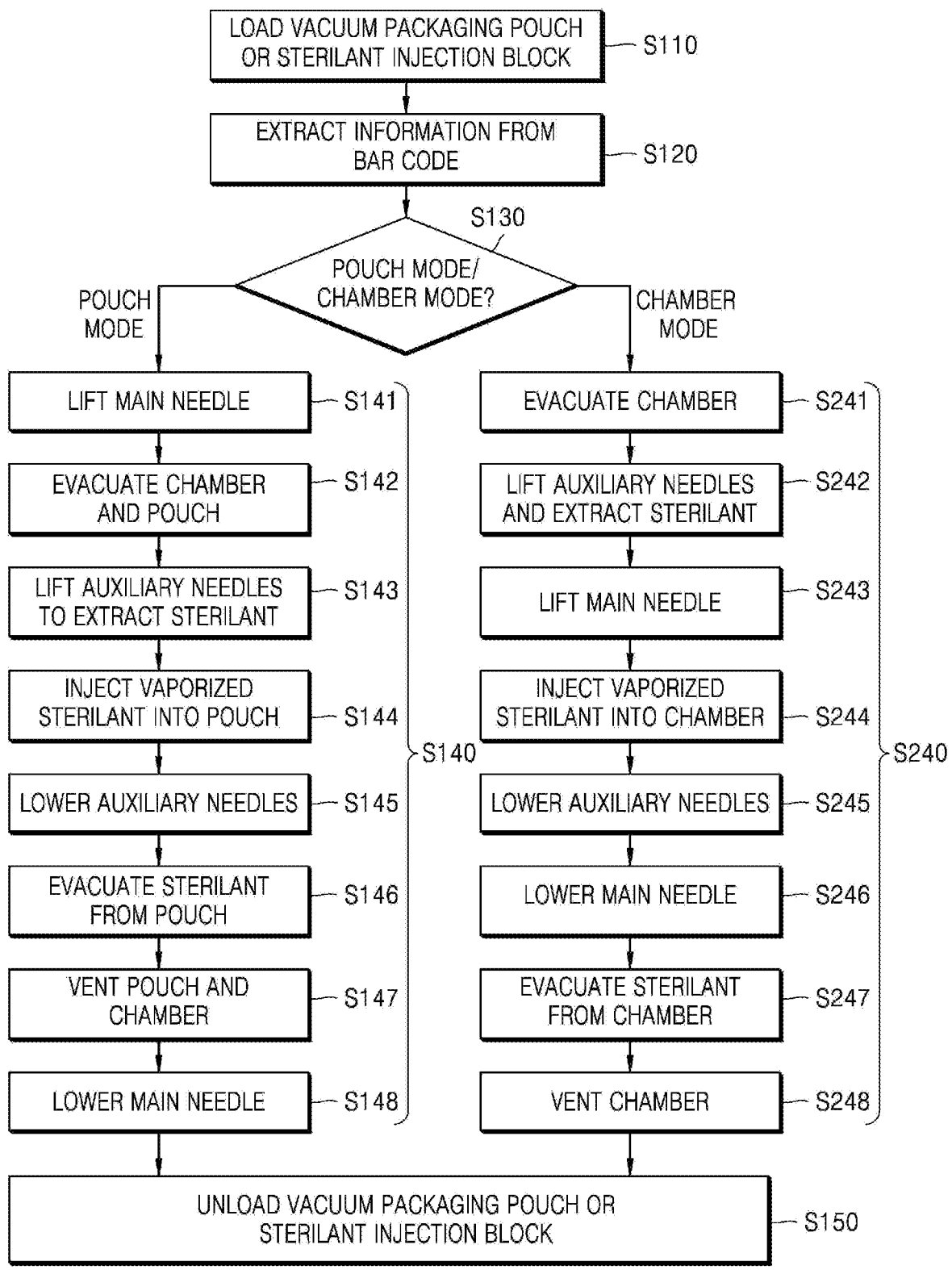
FIG. 6 is a flowchart illustrating a sterilization method according to an embodiment of the present invention.

FIG. 6 is a flowchart illustrating a sterilization method according to an embodiment of the present invention.

Referring to FIGS. 5 and 6, the sterilization method includes: operation S110 in which the sterilant injection block 12 for containing the sterilant 228 and providing the sterilant injection path 225 for injecting the sterilant or the vacuum packaging pouch 10 having the sterilant injection block 12 is mounted inside the vacuum chamber 120; and operations S140 and S150 in which the vacuum chamber 120 is operated in a chamber mode in which the vacuum chamber 120 is used as a sterilization container when only the sterilant injection block 12 is mounted and the vacuum packaging pouch 10 is operated in a pouch mode in which the vacuum packaging pouch 10 is used as a sterilization container when the vacuum packaging pouch is mounted.

In operation S150, after the chamber mode or the pouch mode is completed, the vacuum packaging pouch 10 or the sterilant injection block 12 is unloaded. The sterilant may be hydrogen peroxide.

In operation S120, the sterilant injection block 12 has a bar code or a QR code, and the code reader 184 may extract information recorded in the bar code or a QR code 229.

In operation S130, a sterilization process may be performed in the chamber mode or the pouch mode according to the information recorded in the bar code or the QR code. In the chamber mode, the vacuum chamber is used as a sterilization container into which a sterilant is injected. Meanwhile, in the pouch mode, the vacuum packaging pouch is used as a sterilization container into which a sterilant is injected.

The chamber mode in operation S240 includes: operation S241 of evacuating the vacuum chamber; operation S242 of lifting an auxiliary needle to extract a sterilant from the sterilant injection block; operation S243 of lifting a main needle; operation S244 of vaporizing the extracted sterilant and injecting the vaporized sterilant into the vacuum chamber through the main needle; operation S245 of lowering the auxiliary needle; operation S246 of lowering the main needle; and operation S247 of venting the vacuum chamber.

The chamber mode will be described in detail. The sterilant injection block 12 is mounted inside the vacuum chamber 120 and at the same time the object is contained inside the vacuum chamber 120. In operation S120, information of a bar code attached to the sterilant injection block 12 is read, in operation S130, it is determined whether the information is related to the chamber mode or the pouch mode, and a sterilization process is performed.

The heating block 185 may press the sterilant injection block 12 to heat the same.

In operation S241, the first valve 161 and the sixth valve 166 are opened, and the vacuum chamber 120 is evacuated to a pressure of several tens Torr or less.

In operation S242, the first valve 161 and the sixth valve 166 are closed, a second valve 162 or a third valve 163 is opened, and the auxiliary needles 192a and 196a are lifted and a sterilant is extracted from the sterilant containers 224 and 226 through the sterilant container stoppers 224a and 226a. The sterilant 228 may be extracted from the sterilant containers 224 and 226 and provided to the vaporizer 130.

In operation S243, the main needle 194a may be lifted. Accordingly, the main needle 194a may penetrate the sterilant injection path stopper 225a.

In operation S244, the extracted sterilant may be vaporized and injected into the vacuum chamber 120 through the main needle 194a. The sterilant provided through the vaporizer 130 and the main needle 194a may be diffused into the vacuum chamber 120. The sterilant diffused into the vacuum chamber may permeate a selectively permeable film to sterilize a packaged object to be treated.

In operation S245, the second valve 162 and the third valve 163 may be closed before the auxiliary needle 192a is lowered. Thereafter, the auxiliary needles 192a and 196a may be lowered. The vacuum chamber 120 may maintain sealing with the auxiliary needles 192a and 196a even when the auxiliary needles 192a and 196a are lowered.

In operation S246, the main needle 194a may be lowered. The vacuum chamber 120 may maintain sealing with the main needle 194a even when the main needle is lowered.

In operation S247, the sterilant may be evacuated from the vacuum chamber 120. In order to evacuate the sterilant from the vacuum chamber, the first valve 161 and the sixth valve 166 may be opened. Accordingly, the vacuum pump 140 may evacuate the sterilant in the vacuum chamber to the outside. The sterilant decomposition unit 143 disposed at a front end of the vacuum pump 140 decomposes a sterilant such as hydrogen peroxide into plasma, and the decomposed harmless gas may be evacuated to the outside through the vacuum pump.

In operation S248, the vacuum chamber 120 may be vented. In order to vent the vacuum chamber to atmospheric pressure, the sixth valve 166 may be closed and a fifth valve 165 and the first valve 161 may be opened. Accordingly, the air filtered through the filter 150 may be provided inside the vacuum chamber 120 to maintain the vacuum chamber 120 at atmospheric pressure.

The pouch mode will be described in detail.

The pouch mode in operation S140 includes: operation S141 of lifting a main needle; operation S142 of evacuating the vacuum chamber and evacuating the vacuum packaging pouch through the main needle; operation S143 of lifting an auxiliary needle to extract a sterilant from the sterilant injection block; operation S144 of vaporizing the extracted sterilant and injecting the sterilant into the vacuum packaging pouch through the main needle; operation S145 of lowering the auxiliary needle; operation S146 of evacuating the sterilant from the vacuum packaging pouch through the main needle; operation S147 of venting the vacuum chamber and venting the vacuum packaging pouch using the main needle; and operation S148 of lowering the main needle. In the pouch mode, the vacuum packaging pouch 10 having the sterilant injection 12 is prepared.

The heating block 185 may press the sterilant injection block 12 to heat the same.

In operation S141, the main needle 194a is lifted. Accordingly, the main needle may pass through the sterilant injection path stopper 225a.

In operation S142, the vacuum chamber 120 is evacuated and the vacuum packaging pouch 10 is evacuated through the main needle. The vacuum chamber 120 is evacuated by the vacuum pump 140 in a state where the first valve 161 and the sixth valve 166 are opened. Also, the vacuum packaging pouch 10 is evacuated by the vacuum pump 140 in a state where the second valve 162 and the third valve 163 are closed and the fourth valve 164 is opened. The vacuum chamber 140 and the vacuum packaging pouch 10 may be simultaneously evacuated. The first valve 161 and the fourth valve 164 are closed when pressures of the vacuum chamber 120 and the vacuum packaging pouch 10 are reduced to certain pressures (about several Torr) or less.

In operation S143, the auxiliary needles 192a and 196a are lifted to extract a sterilant from the sterilant injection block 12. In this case, the second valve 162 or the third valve 163 may be opened.

In operation S144, the extracted sterilant may be vaporized and injected into the vacuum packaging pouch 10 through the main needle 194a. The extracted sterilant may be supplied to the vaporizer 130 and vaporized, and the vaporizer 130 may provide the vaporized sterilant to the main needle 194a. The main needle 194a may inject the sterilant into the vacuum packaging pouch through the sterilant injection path 225. Here, the vacuum packaging pouch 10 is maintained in a vacuum state at a certain pressure. However, since the pressure of the vacuum packaging pouch is higher than that of the vacuum chamber, the vacuum packaging pouch may be expanded to ensure a certain volume. The sterilant may diffuse into the vacuum packaging pouch by the pressure difference. As the sterilant is injected into the vacuum packaging pouch, an internal pressure of the vacuum packaging pouch increases, and the volume of the vacuum packaging pouch having a high pressure with respect to the vacuum chamber maintained in a vacuum state may increase. An object to be treated disposed inside the vacuum packaging pouch is sterilized by the sterilant.

In operation S145, when the sterilization process is completed, the auxiliary needles 192a and 196a are lowered. Even when the auxiliary needles 192a and 196a are lowered, sealing between the auxiliary needle and the vacuum chamber may be maintained. In this case, the second valve 162 and the third valve 163 may be closed.

In operation S146, the sterilant may be evacuated from the vacuum packaging pouch 10 through the main needle 194a. After the sterilization process is completed, the fourth valve 164 and the sixth valve 166 may be opened to remove the sterilant from the vacuum packaging pouch 10. Accordingly, the vacuum pump 140 may exhaust the sterilant in the vacuum packaging pouch 10 through the main needle and the sterilant injection path. In this case, the sterilant decomposition unit 143 may decompose the sterilant which is hydrogen peroxide by using plasma. The decomposed sterilant may be evacuated to the outside through the vacuum pump.

In operation S147, the vacuum chamber 120 is vented and the vacuum packaging pouch 10 is vented using the main needle. The sixth valve 166 is closed, and the fifth valve 165 and the fourth valve 164 may be opened. The air filtered through the filter 150 may be supplied to the vacuum chamber 120 through the fifth valve 165 and the first valve 161. In addition, the air filtered through the filter may be supplied to the vacuum package through the fifth valve 165, the fourth valve 164, the main needle 194a, and the sterilant injection path 225. Accordingly, pressures of the vacuum package and the vacuum chamber may be an atmospheric pressure.

In operation S148, the main needle 194a may be lowered. The vacuum packaging pouch may then be unloaded from the vacuum chamber.

According to a modified embodiment of the present invention, the sterilization apparatus may be set to operate in the chamber mode only or in the pouch mode only.

The case where the sterilization apparatus operates in the chamber mode only will be described.

A sterilization method of the sterilization apparatus includes: mounting the sterilant injection block 12 inside the vacuum chamber 120 to receive a sterilant and provide a sterilant injection path for injecting the sterilant; vacuum evacuating the interior of the vacuum chamber 120; extracting the sterilant from the sterilant injection block 12 and injecting the sterilant into the vacuum chamber through the sterilant injection block 12 to sterilize an object to be treated disposed in the vacuum chamber; and evacuating the sterilant from the vacuum chamber 120.

The sterilization method may further include: heating the sterilant injection block 12 in the vacuum chamber; and venting the vacuum chamber to an atmospheric pressure after evacuating the sterilant. The sterilant may be hydrogen peroxide. The sterilant may be vaporized and injected into the vacuum packaging pouch through the sterilant injection block. The sterilant injection block may include a bar code or a QR code, and may perform a sterilization process according to information recorded in the bar code or the QR code.

The case where the sterilization apparatus operates in the pouch mode only will be described.

A sterilization method of the sterilization apparatus includes: mounting the vacuum packaging pouch 10, which has the sterilant injection block 12 for containing the sterilant and providing a sterilant injection path for injecting the sterilant, inside the vacuum chamber; vacuum evacuating the interior of the vacuum chamber 120 and the vacuum packaging pouch 10; extracting the sterilant from the sterilant injection block and injecting the sterilant into the vacuum packaging pouch through the sterilant injection block to sterilize an object to be treated disposed in the vacuum packaging pouch; and evacuating the sterilant from the vacuum packaging pouch 10.

The sterilization method may further include: heating the sterilant injection block 12 in the vacuum chamber; and venting the vacuum chamber to an atmospheric pressure after evacuating the sterilant. The sterilant may be hydrogen peroxide and may be vaporized and injected into the vacuum packaging pouch through the sterilant injection block. The sterilant injection block may include a bar code or a QR code, and may perform a sterilization process according to information recorded in the bar code or the QR code.

Figure 7A:
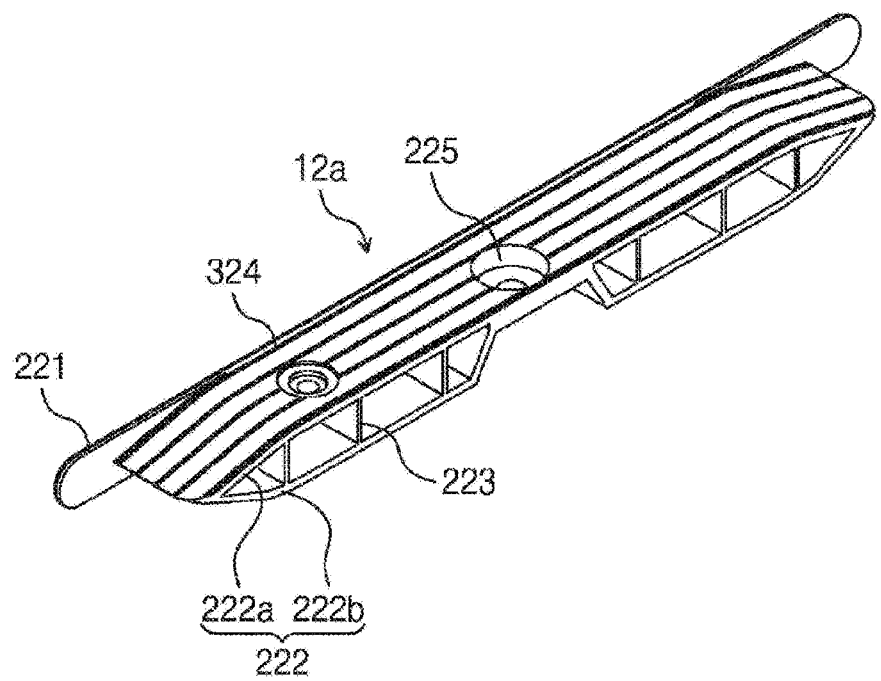
FIG. 7A is a perspective view of a sterilant injection block according to another embodiment of the present invention.

FIG. 7A is a perspective view of a sterilant injection block according to another embodiment of the present invention.

Figure 7B:
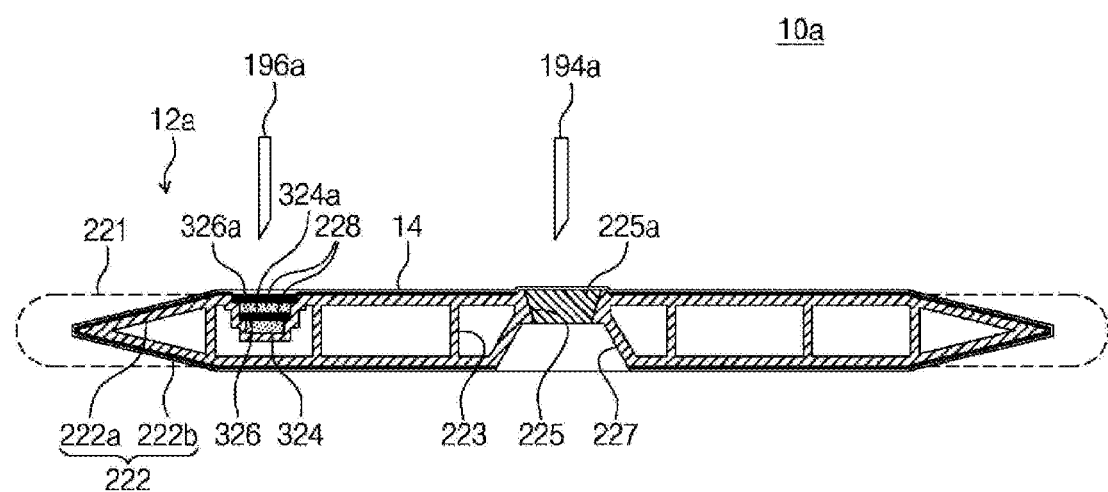
FIG. 7B is a cross-sectional view of the sterilant injection block of FIG. 7A.

FIG. 7B is a cross-sectional view of the sterilant injection block of FIG. 7A.

Referring to FIGS. 7A and 7B, the vacuum packaging pouch 10 may include a sterilant injection block 12a for containing an object to be treated therein and being sealed to be in a vacuum state, and vacuum evacuating and injecting a sterilant from the outside.

The sterilant injection block 12a may include: the upper strip 222a and the lower strip 222b having opposite ends bent to contact each other and the central portions extending parallel to each other; the barrier wall 223 between the upper strip and the lower strip; the sterilant injection path 225 formed through the upper strip; the sterilant injection path stopper 225a on the upper strip to block the sterilant injection path; and the alignment strip 221 extending laterally along one side of the upper strip and the lower strip to seal the one side of the upper strip and the lower strip. An upper surface of the upper strip and a lower surface of the lower strip may be sealed at one end of the vacuum packaging pouch 10.

The sterilant injection block 12a may include: a first sterilant container 326 disposed apart from the sterilant injection path 225 and containing the sterilant 228 and being sealed; a first sterilant container stopper 326a of an elastic material disposed on the upper strip 222a and blocking the first sterilant container 326; a second sterilant container 324 disposed at a lower portion of the first sterilant container stopper and containing the sterilant 228 and being sealed; and a second sterilant container stopper 324a of an elastic material disposed between the first sterilant container 326 and the second sterilant container 324. The second sterilant container stopper 324a and the first sterilant container stopper 326a may be films or plates of an elastic material such as silicone rubber.

The auxiliary needle 196a penetrates the first sterilant container stopper 326a to extract the sterilant and successively extract the sterilant through the second sterilant container stopper 324a. As a result, the number of auxiliary needles for sterilant extraction may be reduced.

Figure 8:
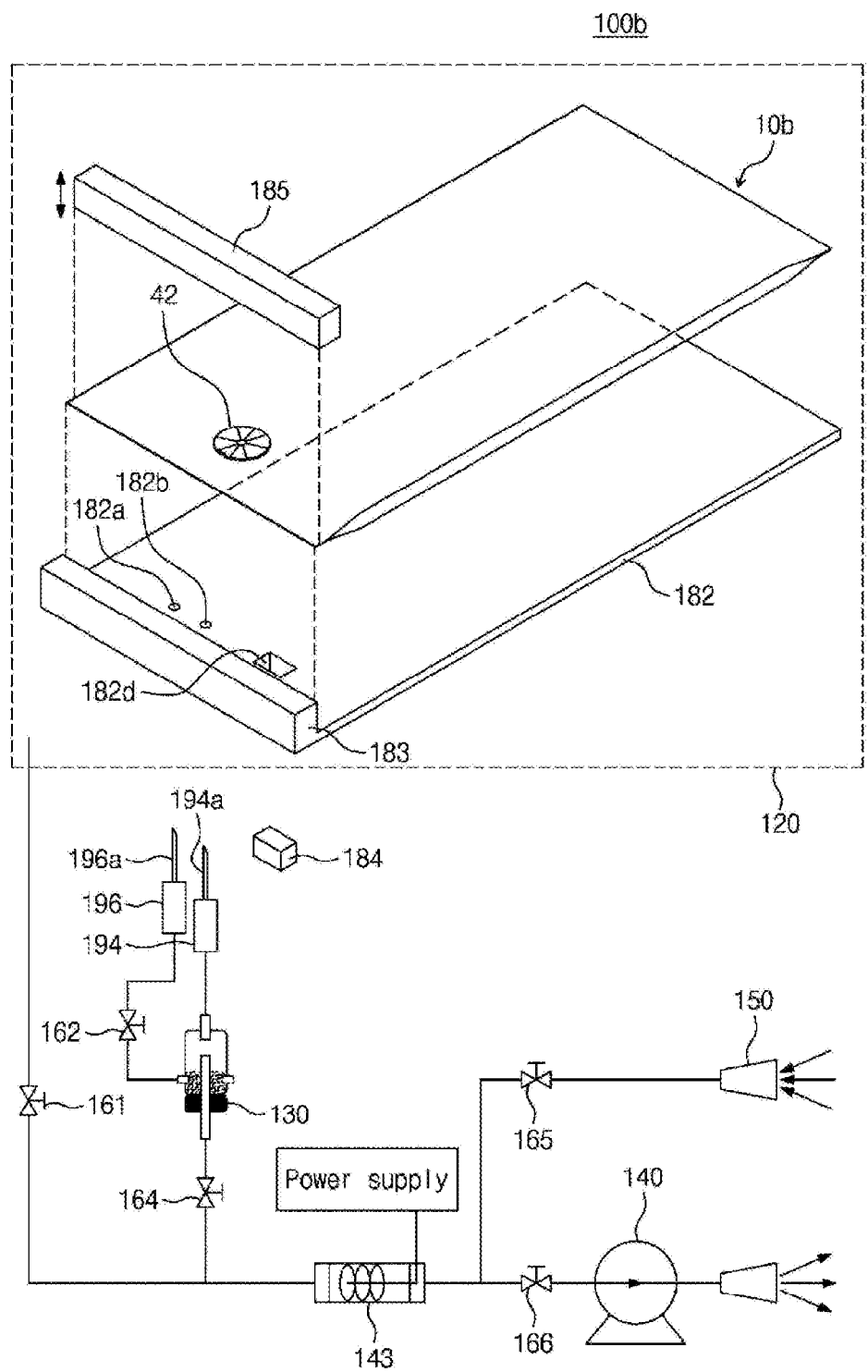
FIG. 8 is a conceptual diagram of a sterilization apparatus according to another embodiment of the present invention.

FIG. 8 is a conceptual diagram of a sterilization apparatus according to another embodiment of the present invention.

FIG. 9A is a plan view of a vacuum packaging pouch used in the sterilization apparatus of FIG. 8.

Figure 9B:
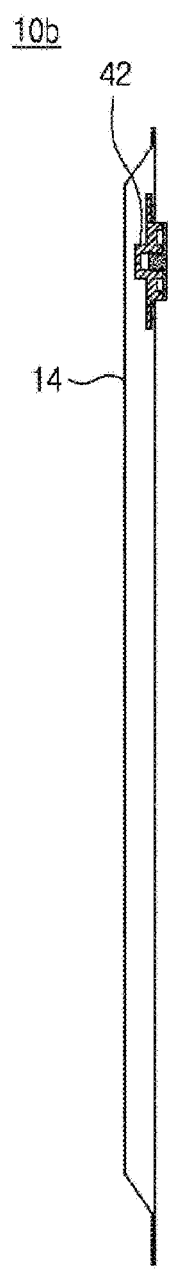
FIG. 9B is a sectional view of a vacuum packaging pouch used in the sterilization apparatus of FIG. 8.

FIG. 9B is a sectional view of a vacuum packaging pouch used in the sterilization apparatus of FIG. 8.

Figure 10A:
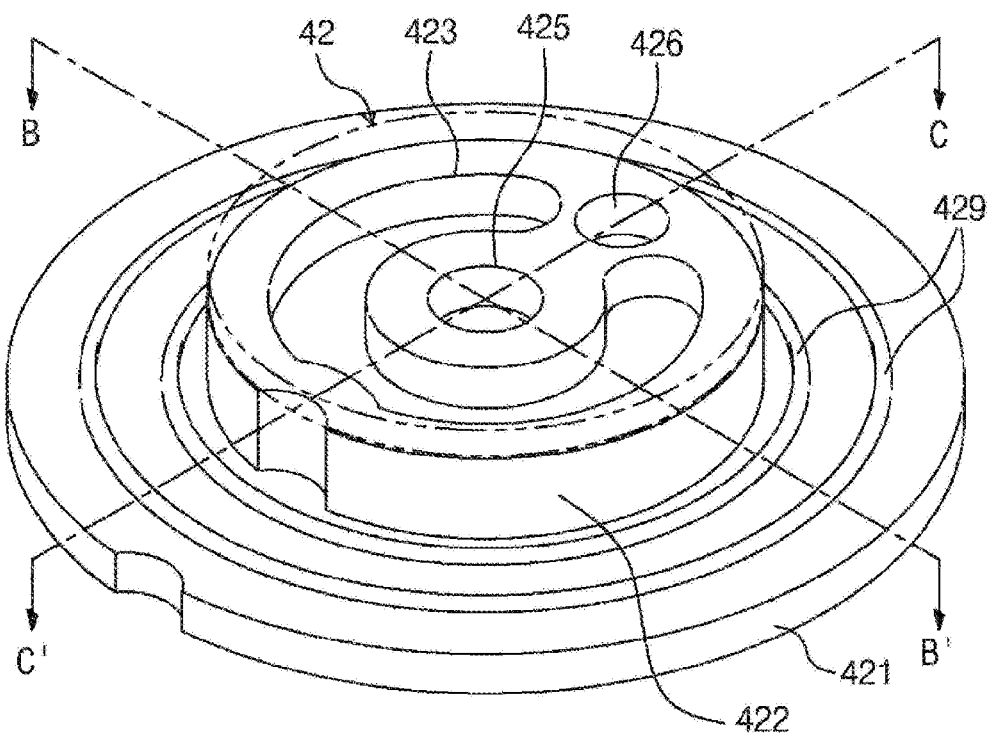
FIG. 10A is a perspective view of a sterilant injection block of the vacuum packaging pouch of FIG. 9A.

FIG. 10A is a perspective view of a sterilant injection block of the vacuum packaging pouch of FIG. 9A.

Figure 10B:
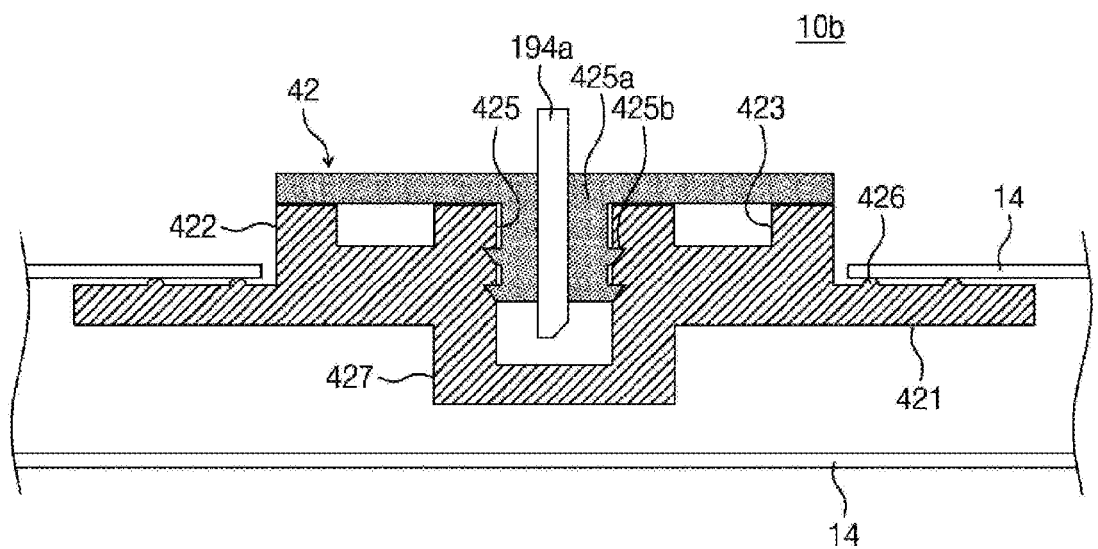
FIG. 10B is a cross-sectional view taken along a line B-B' of the sterilant injection block of the vacuum packaging pouch of FIG. 10A.

FIG. 10B is a cross-sectional view taken along a line B-B' of the sterilant injection block of the vacuum packaging pouch of FIG. 10A.

Figure 10C:
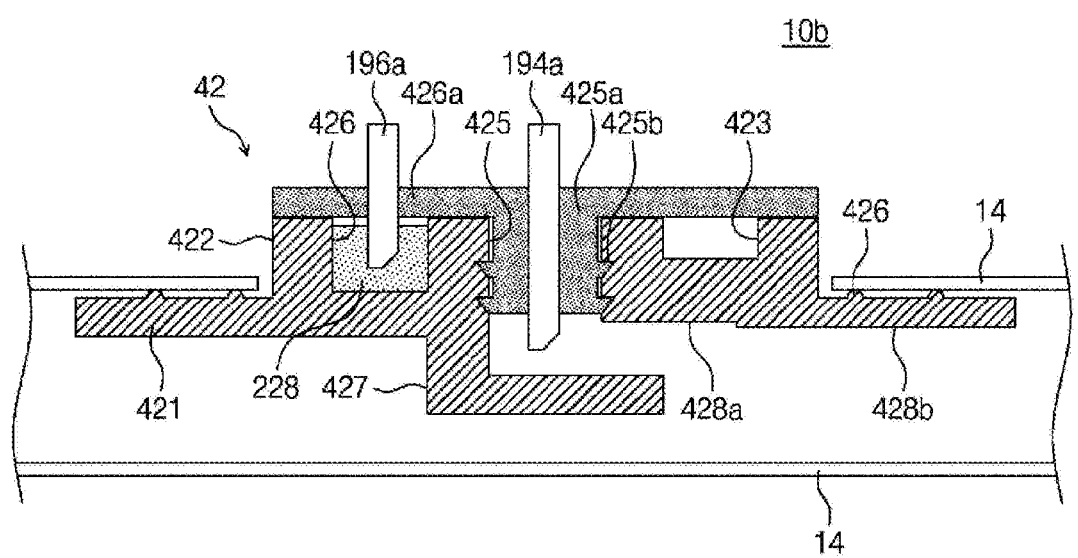
FIG. 10C is a cross-sectional view taken along a line C-C' of the sterilant injection block of the vacuum packaging pouch of FIG. 10A.

FIG. 10C is a cross-sectional view taken along a line C-C' of the sterilant injection block of the vacuum packaging pouch of FIG. 10A.

Referring to FIGS. 8 to 10, a sterilization apparatus 100b includes: a vacuum packaging pouch 10b having a sterilant injection block 42 for containing an object to be treated (not shown) therein and being sealed to be in a vacuum state, and vacuum evacuating and injecting a sterilant from the outside; the vacuum chamber 120 having the door 124 and containing the vacuum packaging pouch 10b; the main needle 194a for injecting a sterilant into the vacuum packaging pouch 10b and vacuum evacuating the vacuum packaging pouch 10b; and the vacuum pump 140 for evacuating the vacuum packaging pouch 10b or the vacuum chamber 120. The sterilant injection block 42 is sealed with the vacuum packaging pouch 10b.

The vacuum chamber 120 may include the door 124 and a chamber body 122. The door 124 may be a cover of the vacuum chamber 120. The door 124 may be coupled to the vacuum chamber 120 by a rotating unit such as a hinge.

The vacuum chamber 120 may have a space for containing the vacuum packaging pouch 10b and the heating block 185 therein. The vacuum chamber 120 may have a rectangular parallelepiped shape and may be formed of metal.

The vacuum chamber 120 may be connected to the vacuum pump 140 through a connection pipe. The vacuum pump 140 may vacuum evacuate the vacuum chamber 120 and the vacuum packaging pouch 10b.

The filter 150 may suck in the air to remove fine dust and bacteria and provide the air to the vacuum chamber 120 or the vacuum packaging pouch 10b.

The vaporizer 130 may vaporize the sterilant and inject the sterilant into the vacuum packaging pouch 10b. When the sterilant is hydrogen peroxide, the vaporizer 130 may heat and vaporize the sterilant at a temperature of 50° C. to 110° C. and may inject the vaporized sterilant into the vacuum packaging pouch 10b. The vaporizer 130 may be disposed outside the vacuum chamber.

The heating block 185 may be disposed within the vacuum chamber and may contact the sterilant injection block 42 to heat the sterilant injection block 42. The heating block 185 is heated from 50° C. to 110° C. and may heat some or all of the vacuum packaging pouch. The heating block 185 may be mounted on the door 124 of the vacuum chamber to be vertically movable.

When the vacuum chamber 120 is vacuum evacuated, heat transfer through the air is impossible. Therefore, the heating block 185 may be pressed to directly contact the vacuum packaging pouch 10b or the sterilant injection block 42. The heating block 185 may be in the shape of a rod having a rectangular cross section. The inside of the heating block 185 may be heated by a heating wire. The heating block 185 may press and heat the sterilant injection block 12 of the vacuum packaging pouch 10b.

The lower surface 182 of the vacuum container may align and support the vacuum packaging pouch 10b. Furthermore, the lower surface 182 of the vacuum container is plate-shaped and may include a plurality of openings 182a, 182b, and 182d to allow access to the sterilant injection block 12. The lower surface 182 of the vacuum container may include the alignment portion 183 protruding for alignment of the vacuum packaging pouch 10. The lower surface 182 of the vacuum container is formed of metal or an insulator, and may be heated so as to be maintained at a constant temperature. The lower surface 182 of the vacuum container may be fixed in the vacuum chamber 120. The lower surface 182 of the vacuum container may be disposed inside the vacuum chamber to support the vacuum packaging pouch and provide the main needle opening 182b through which the main needle 194a can pass.

A sealing unit on the lower surface 182 of the vacuum container may seal around the sterilant injection path 425. The sealing unit may be an O-ring. The main needle transfer portion includes an auxiliary sealing unit which is in contact with the lower surface 182 of the vacuum container around the opening 182b for a main needle to perform sealing.

The main needle 194a may be arranged to pass through the opening 182b for a main needle in a lower surface of the vacuum container. An end of the main needle 194a is obliquely processed like a typical needle, and an opening (not shown) may be formed in a side surface of the end of the main needle 194a. A fluid path may be provided through an opening of the main needle. The main needle 194a may provide a path for exhausting air from the vacuum packaging pouch and may provide a path for supplying a sterilant from the outside to the inside of the vacuum packaging pouch. An inner diameter of the main needle 194a may be at least 0.5 mm or more. The inner diameter of the main needle may be sufficiently short and large to provide sufficient conductance for vacuum evacuation. A length of the main needle may be a few centimeters or less and the inner diameter of the main needle may be 0.5 mm or more. A material of the main needle may be metal or a metal alloy.

The main needle transfer portion 194 may provide vertical linear motion to the main needle 194a and may be disposed inside the vacuum container 120.

The auxiliary needle 196a may extract a sterilant sealed in the vacuum packaging pouch 10b. The auxiliary needles 196a and 192a may extract a liquid sterilant contained in a sterilant container of the vacuum packaging pouch. The main needle transfer portion may provide vertical linear motion to the main needle and may be disposed inside the vacuum container.

Auxiliary needle transfer portions 196 and 192 provide linear motion to the auxiliary needle 196a and may be disposed outside the vacuum container.

The vacuum packaging pouch 10b is made of an NY and/or PE material having sufficient flexibility and may be in the form of a bag sealed in a film form. The vacuum packaging pouch 10b may include the vacuum packaging bag 14 and the sterilant injection block 42 disposed at one surface of the vacuum packaging bag. The other end of the vacuum packaging pouch 10b is initially opened, and after an object to be treated (e.g., a medical device) is inserted, the other end of the vacuum packaging pouch may be sealed by a method such as thermocompression bonding so as to include a thermocompression bonding strip. The vacuum packaging pouch 10b may include the sterilant injection block 42 for vacuum evacuation and injecting a sterilant from the outside. The vacuum packaging bag 14 may be made of polyethylene. The vacuum packaging bag 14 may include a lower film and an upper film which provide an internal space by edge thermocompression bonding.

The sterilant injection block 42 may include the same material as that of the vacuum packaging bag. The material of a surface of the sterilant injection block 42 may be the same as the material of the vacuum packaging bag. Accordingly, the sterilant injection block 42 may be inserted into an opening and thermally compressed with the vacuum packaging bag 14 to provide a sealed space.

The sterilant injection block 42 may include the sterilant injection path 425; and a sterilant injection path stopper 425a of an elastic material blocking the sterilant injection path. The sterilant injection path stopper 425a may be made of an elastic material such as silicone rubber. The sterilant injection path stopper 425a may be fixed by fitting and/or an adhesive. Thus, even when the main needle 194a pierces the sterilant injection path stopper 425a and then retreats, the sterilant injection path stopper 425a may sufficiently seal the vacuum packaging pouch. After the sterilization process is completed, even when the vacuum packaging pouch is exposed to the polluted atmosphere for a long time, the sterilant injection path stopper 425a may prevent infiltration of bacteria.

The main needle 194a may pierce the sterilant injection path stopper 425a. A material of the sterilant injection path stopper 425a may be silicone rubber or an elastic polymer material. When the main needle 194a pierces the sterilant injection path stopper 425a, the sterilant injection path stopper 425a may maintain a sealed state by elasticity. When fluid flows through the main needle 194a, the fluid may not leak through the sterilant injection path stopper 425a.

The sterilant injection block 42 may include a sterilant container 426 for containing the sterilant 228 and being sealed; and a sterilant container stopper 426a of an elastic material blocking the sterilant container 426. The auxiliary needle 196a may pierce the sterilant container stopper 426a to extract the sterilant. The vaporizer 130 vaporizes the sterilant 228 extracted through the auxiliary needle and the vaporized sterilant may be injected into the vacuum packaging pouch 10b through the main needle 194a and the sterilant injection path 225.

The sterilant injection block 42 may include: a disk-shaped sealing plate 421; an upper protrusion 422 protruding from an upper surface of the sealing plate; a lower protrusion 427 protruding from a lower surface of the sealing plate; the sterilant injection path 425 passing through the upper protrusion 422 and the sealing plate 421 and opened to a side surface of the lower protrusion 427; and the sterilant injection path stopper 425a blocking the sterilant injection path 425 on an upper surface of the upper protrusion. An upper surface of an edge of the sealing plate 421 may be thermally compressed with an opening of the vacuum packaging pouch. A material of the sterilant injection block 42 may be a PE material except for a stopper. The sterilant injection block 42 may be integral. At the side surface of the lower protrusion, the sterilant injection path 425 may be connected to a first trench 428a and a second trench 428b extending radially from the lower surface of the sealing plate. The first trench 428a and the second trench 428b may provide a fluid path to the sterilant injection path 425 even when the vacuum packaging pouch is pressed by a pressure difference between inside and outside.

The sterilant injection block 42 may further include: a sterilant container 426 disposed in the upper protrusion 422 and containing the sterilant 228 and being sealed; and a sterilant container stopper 426a of an elastic material disposed in the upper protrusion and blocking the sterilant container. The sterilant container stopper 426a and the sterilant injection path stopper 425a may be integrated and made of an elastic material. The sterilant injection path stopper 425a may have a disk shape and may include a ring shaped protrusion 425b having a triangular cross section on a side of the disk shape. The protrusion 425b may be engaged with a groove formed in the sterilant injection path 225 and inserted. The sterilant container stopper 426a and the sterilant injection path stopper 425a may be additionally fixed to the upper protrusion 422 by an adhesive or the like. The upper protrusion 422 may include a trench 423 for reducing weight. The upper protrusion and the lower protrusion may have a disc shape. The sealing plate 421 may include a ring-shaped protrusion 429 for thermocompression bonding with a vacuum packaging pouch.

The code adhesive tape 229 having code such as a bar code or a QR code to be printed may be attached to the vacuum packaging pouch 10b or the sterilant injection block 42. It is possible to perform a reliable sterilization process by transmitting information about the amount of sterilant injected by using the code adhesive tape 229, the type of packaging container, date of manufacture, etc. to the sterilizer. The code reader 184 may extract the information of the code adhesive tape 229 through the opening 182d formed in a support plate of the vacuum packaging pouch.

The sterilization apparatus may include the plurality of valves 161 to 166. The valve may be used to evacuate the vacuum packaging pouch and the vacuum chamber, to inject a sterilant to the vacuum packaging pouch, and to vent the vacuum packaging pouch and the vacuum chamber to the atmosphere.

Figure 11:
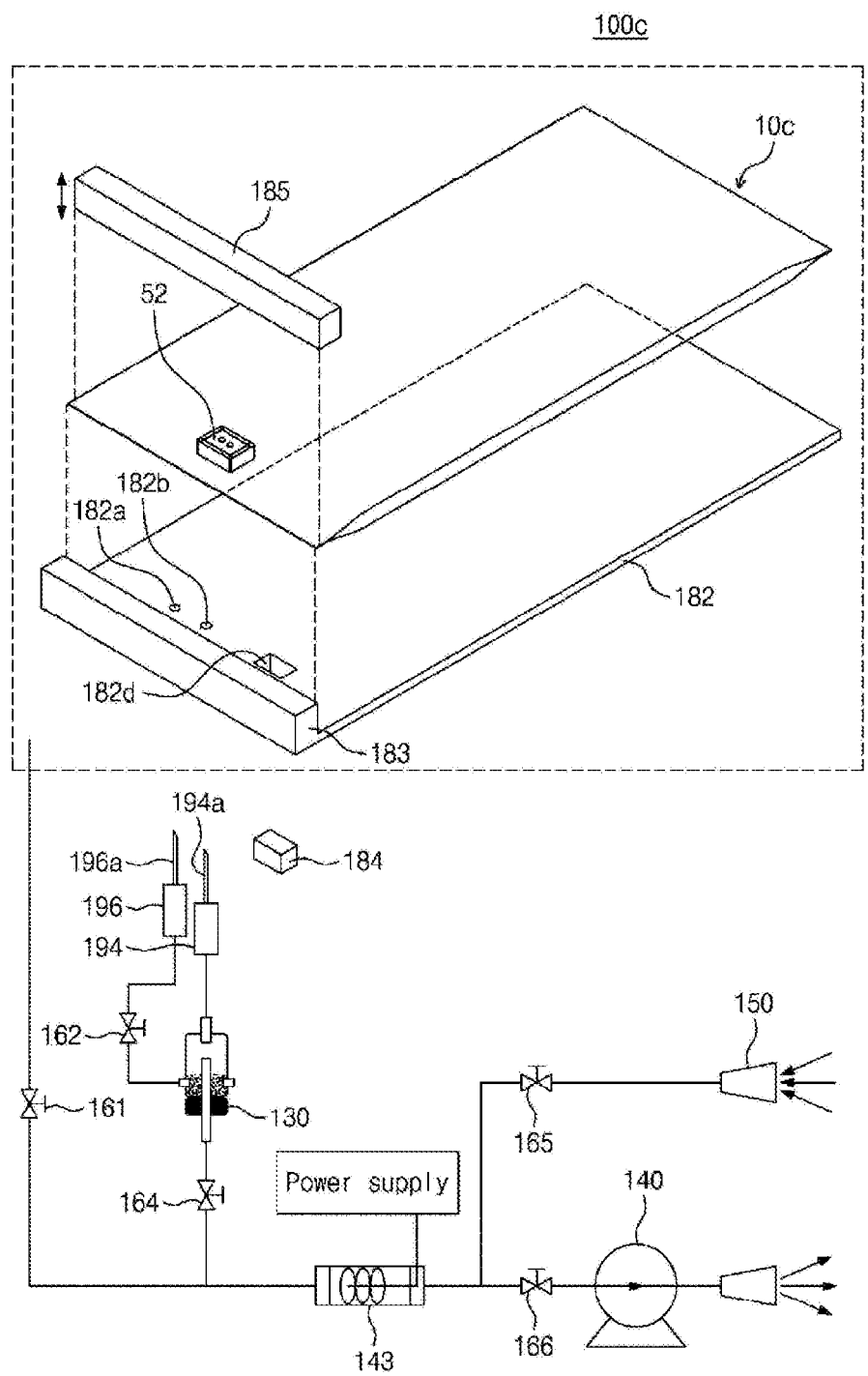
FIG. 11 is a conceptual diagram of a sterilization apparatus according to another embodiment of the present invention.

FIG. 11 is a conceptual diagram of a sterilization apparatus according to another embodiment of the present invention.

Figure 12A:
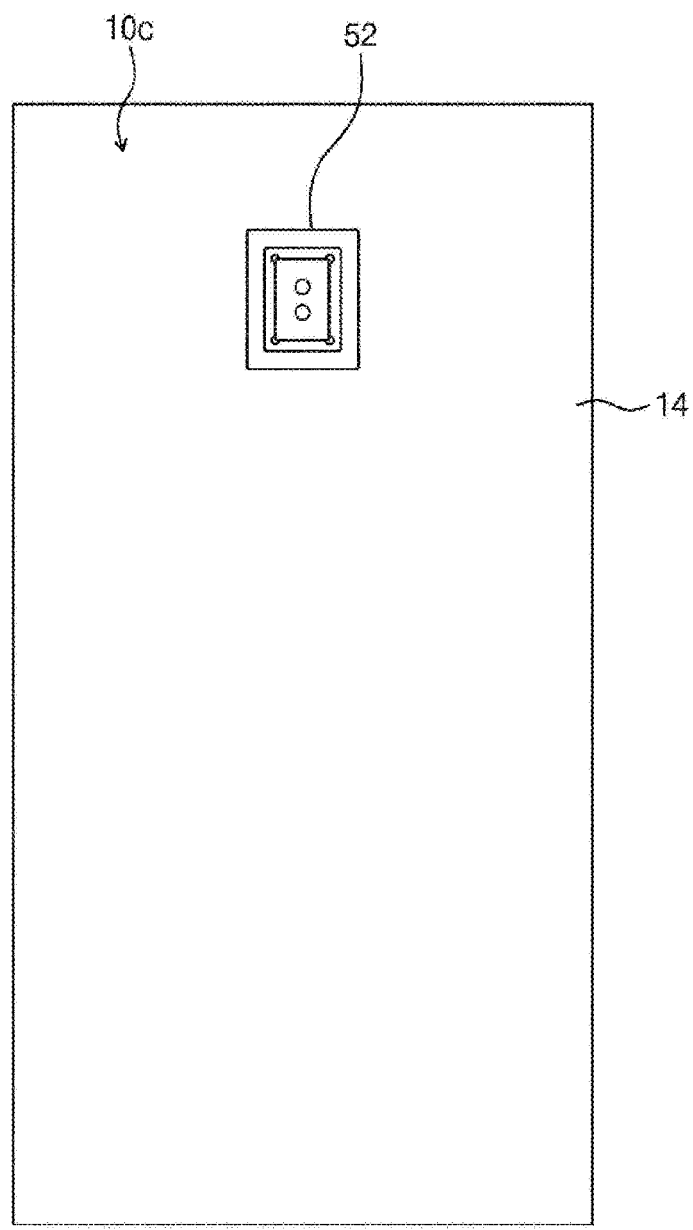
FIG. 12A is a front view of a vacuum packaging pouch of FIG. 11.

FIG. 12A is a front view of a vacuum packaging pouch of FIG. 11.

Figure 12B:
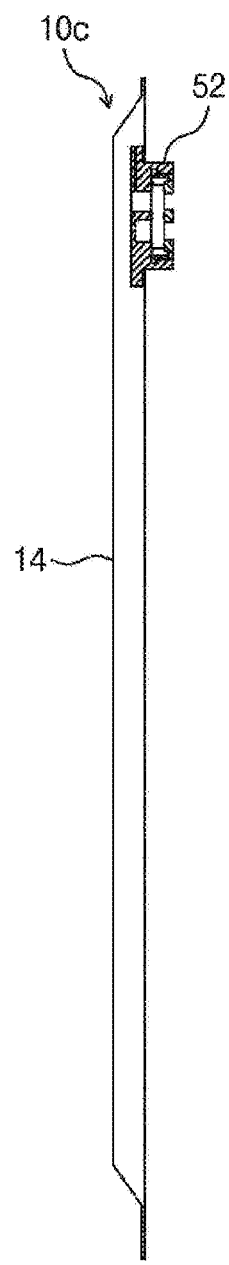
FIG. 12B is a sectional view of the vacuum packaging pouch of FIG. 12A.

FIG. 12B is a sectional view of the vacuum packaging pouch of FIG. 12A.

Figure 13A:
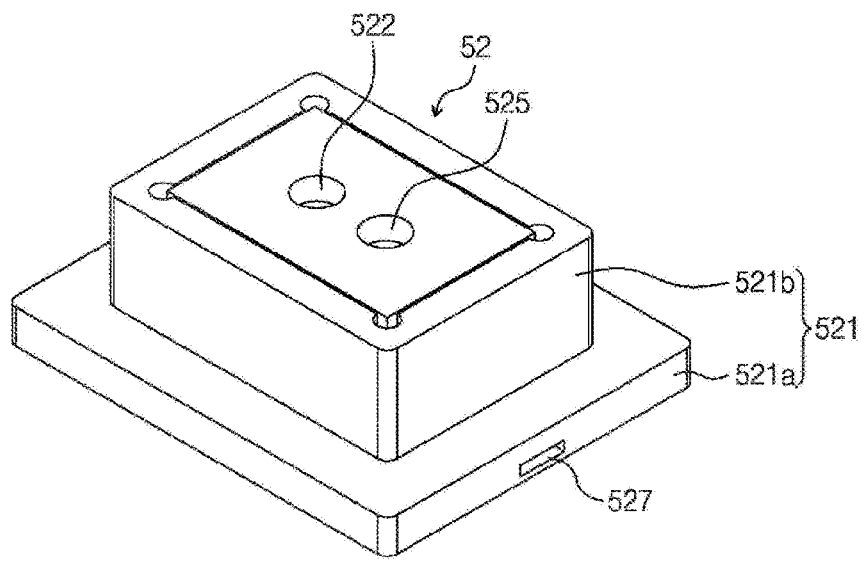
FIG. 13A is a perspective view of a sterilant injection block 52 of the vacuum packaging pouch of FIG. 12A.

FIG. 13A is a perspective view of a sterilant injection block 52 of the vacuum packaging pouch of FIG. 12A.

Figure 13B:
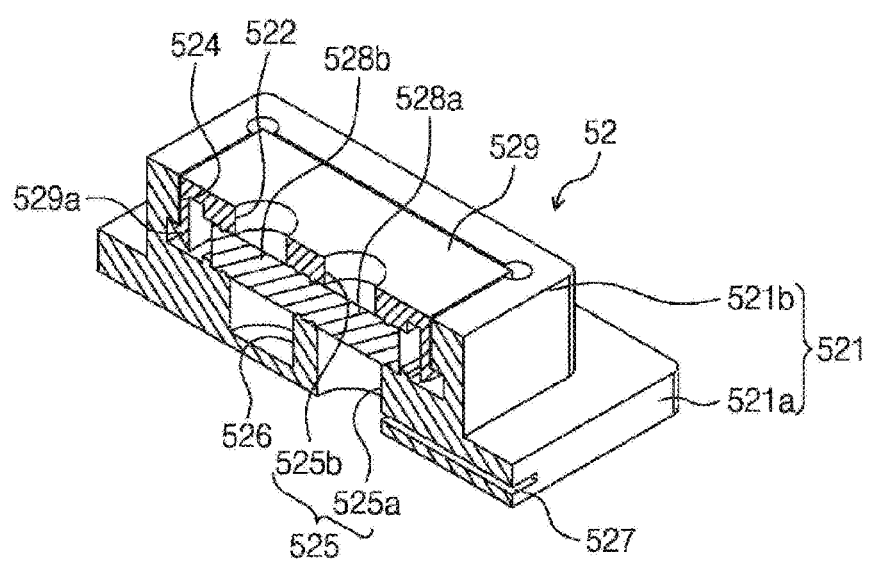
FIG. 13B is a cutaway perspective view of the sterilant injection block 52 of FIG. 13A.

FIG. 13B is a cutaway perspective view of the sterilant injection block 52 of FIG. 13A.

Figure 13C:
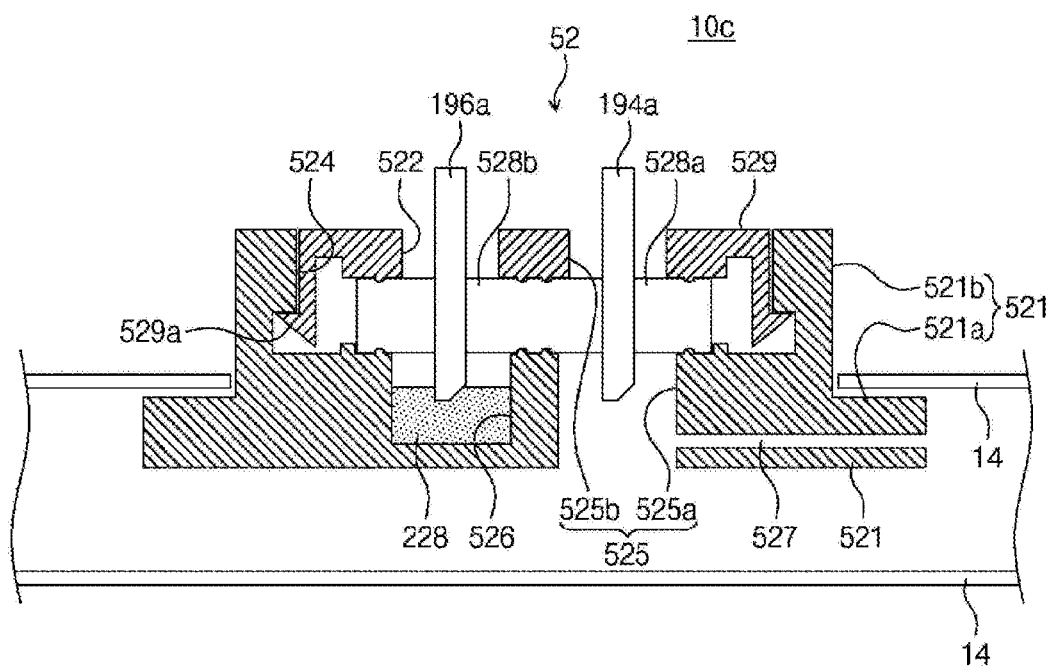
FIG. 13C is a cross-sectional view of the sterilant injection block 52 of FIG. 13A.

FIG. 13C is a cross-sectional view of the sterilant injection block 52 of FIG. 13A.

Referring to FIGS. 11 to 13, a sterilization apparatus 100c includes: a vacuum packaging pouch 10c having the sterilant injection block 52 for containing an object to be treated (not shown) therein and being sealed to be in a vacuum state, and vacuum evacuating and injecting a sterilant from the outside; the vacuum chamber 120 having the door 124 and containing the vacuum packaging pouch 10c; the main needle 194a for injecting a sterilant into the vacuum packaging pouch 10c and vacuum evacuating the vacuum packaging pouch 10c; and the vacuum pump 140 for evacuating the vacuum packaging pouch 10c or the vacuum chamber 120. The sterilant injection block 52 is sealed with the vacuum packaging pouch 10c.

The vacuum chamber 120 may include the door 124 and a chamber body 122. The door 124 may be a cover of the vacuum chamber 120. The door 124 may be coupled to the vacuum chamber 120 by a rotating unit such as a hinge.

The vacuum chamber 120 may have a space for containing the vacuum packaging pouch 10c and the heating block 185 therein. The vacuum chamber 120 may have a rectangular parallelepiped shape and may be formed of metal.

The vacuum chamber 120 may be connected to the vacuum pump 140 through a connection pipe. The vacuum pump 140 may vacuum evacuate the vacuum chamber 120 and the vacuum packaging pouch 10c.

The filter 150 may suck in the air to remove fine dust and bacteria and provide the air to the vacuum chamber 120 or the vacuum packaging pouch 10c.

The vaporizer 130 may vaporize the sterilant and inject the sterilant into the vacuum packaging pouch 10c. When the sterilant is hydrogen peroxide, the vaporizer 130 may heat and vaporize the sterilant at a temperature of 60° C. to 110° C. and may inject the vaporized sterilant into the vacuum packaging pouch 10c. The vaporizer 130 may be disposed outside the vacuum chamber.

The heating block 185 may be disposed within the vacuum chamber and may contact the sterilant injection block 52 to heat the sterilant injection block 52. The heating block 185 is heated from 60° C. to 110° C. and may heat some or all of the vacuum packaging pouch. The heating block 185 may be mounted on the door 124 of the vacuum chamber to be vertically movable.

When the vacuum chamber 120 is vacuum evacuated, heat transfer through the air is impossible. Therefore, the heating block 185 may be pressed to directly contact the vacuum packaging pouch 10c or the sterilant injection block 52. The heating block 185 may be in the shape of a rod having a rectangular cross section. The inside of the heating block 185 may be heated by a heating wire. The heating block 185 may press and heat the sterilant injection block 52 of the vacuum packaging pouch 10c.

The lower surface 182 of the vacuum container is disposed within the vacuum chamber 120 and may align and support the vacuum packaging pouch 10c. Furthermore, the lower surface 182 of the vacuum container is plate-shaped and may include a plurality of openings 182a, 182b, and 182d to allow access to the sterilant injection block. The lower surface 182 of the vacuum container may include the alignment portion 183 protruding for alignment of the vacuum packaging pouch. The lower surface 182 of the vacuum container is formed of metal and may be heated so as to be maintained at a constant temperature. The lower surface 182 of the vacuum container may support the vacuum packaging pouch and provide the opening 182b for a main needle through which the main needle 194a can pass.

The sterilant injection block 52 may include the same material as that of the vacuum packaging bag. The material of a surface of the sterilant injection block 52 may be the same as the material of the vacuum packaging bag. Accordingly, the sterilant injection block 52 may be inserted into an opening and thermally compressed with the vacuum packaging bag 14 to provide a sealed space.

The sterilant injection block 52 may include: the sterilant injection path 525; and a sterilant injection path stopper 528a of an elastic material blocking the sterilant injection path. The sterilant injection path stopper 528a may be made of an elastic material such as silicone rubber. The sterilant injection path stopper 528a may be fixed by a separate cover and/or adhesive. Thus, even when the main needle 194a pierces the sterilant injection path stopper 528a and then retreats, the sterilant injection path stopper 528a may sufficiently seal the vacuum packaging pouch. After the sterilization process is completed, even when the vacuum packaging pouch is exposed to the polluted atmosphere for a long time, the sterilant injection path stopper 528a may prevent infiltration of bacteria.

The main needle 194a may pierce the sterilant injection path stopper 528a. A material of the sterilant injection path stopper 528a may be silicone rubber or an elastic polymer material. When the main needle 194a pierces the sterilant injection path stopper 528a, the sterilant injection path stopper 528a may maintain a sealed state by elasticity. When fluid flows through the main needle 194a, the fluid may not leak through the sterilant injection path stopper 528a.

The sterilant injection block 52 may include: a body portion 521 including a base plate 521a and a protrusion 521b protruding from the base plate; a sterilant injection block cover 529 inserted into a depression 524 recessed in an upper surface of the protrusion 521b; and the sterilant injection path stopper 528a disposed between the sterilant injection block cover 529 and a lower surface of the depression and made of an elastic material. The body portion 521 may include a first through hole 525a passing through the depression and the sterilant injection block cover 529 may include a second through hole 525b aligned with the first through hole 525a. The first through hole 525a and the second through hole 525b may provide the sterilant injection path 525. The upper surface of the base plate 521a may be thermally compressed with an opening of the vacuum packaging pouch.

The base plate 521a may have a rectangular plate shape, and the protrusion may have a rectangular parallelepiped shape. The body portion may be made of PE and may be integral. The depression may be recessed in a rectangular parallelepiped shape. A trench may be formed on a lower side surface of the depression. A hook 529a disposed on a side surface of the sterilant injection block cover 529 may be inserted into the trench and coupled thereto. A lower surface of the sterilant injection block cover 529 is recessed, and the sterilant injection path stopper 528a may be disposed at the recessed portion. The upper surface of the protrusion and the sterilant injection block cover 529 may be substantially flush with each other. The sterilant injection block cover 529 may be made of PE. An auxiliary path 527 passing through the base plate may be formed on a side surface of the first through hole 525a.

The sterilant injection block 52 may further include: a sterilant container 526 disposed on a lower surface of the depression 524 and containing the sterilant; and a sterilant container stopper 528b of an elastic material disposed between the sterilant container 526 and the sterilant injection block cover 529 and blocking the sterilizer container. The sterilant injection block cover 529 includes a third through hole 522 aligned with the sterilant container 526 and the sterilant container stopper 528b and the sterilant injection path stopper 528a may be integrated. The lower surface of the depression may be provided with a locking protrusion such that the sterilant container stopper 528b and the sterilant injection path stopper 528a may be aligned with each other. In addition, a ring-shaped sealing member may be disposed on the lower surface of the depression for sealing. The ring-shaped sealing member may be disposed at the recessed portion of the sterilant injection block cover 529 for sealing.

The auxiliary needle 196a may pierce the sterilant container stopper 528b to extract the sterilant. The vaporizer 130 vaporizes the sterilant 228 extracted through the auxiliary needle and the vaporized sterilant may be injected into the vacuum packaging pouch 10c through the main needle 194a and the sterilant injection path 525.

A code adhesive tape such as a bar code or a QR code to be printed may be attached to the vacuum packaging pouch 10c or the sterilant injection block 52. It is possible to perform a reliable sterilization process by transmitting information about the amount of sterilant injected by using the code adhesive tape, the type of packaging container, date of manufacture, etc. to a sterilizer. A code reader 184 may extract the information of the code adhesive tape 229 through the opening 182d formed on a lower surface of the vacuum chamber.

The sterilization apparatus may include the plurality of valves 161 to 166. The valve may be used to evacuate the vacuum packaging pouch and the vacuum chamber, to inject a sterilant into the vacuum packaging pouch, and to vent the vacuum packaging pouch and the vacuum chamber to the atmosphere.

Figure 14A:
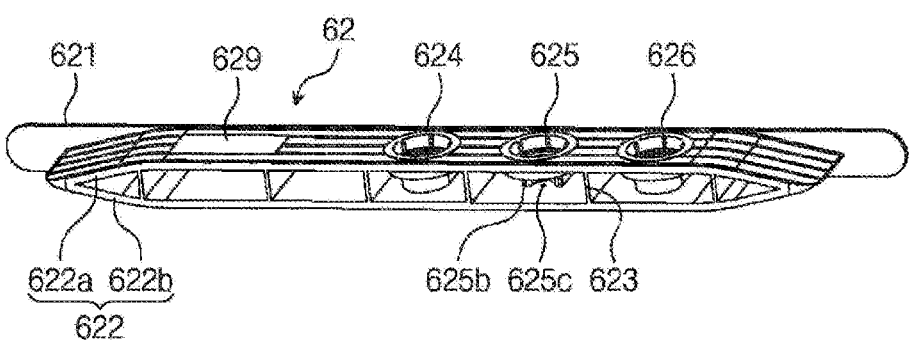
FIG. 14A is a perspective view of a sterilant injection block 62 of a vacuum packaging pouch according to another embodiment of the present invention.

FIG. 14A is a perspective view of a sterilant injection block 62 of a vacuum packaging pouch according to another embodiment of the present invention.

Figure 14B:
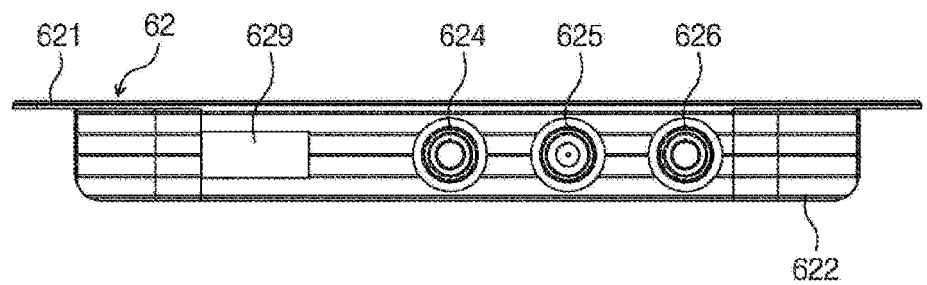
FIG. 14B is a plan view of the sterilant injection block 62 of FIG. 14A.

FIG. 14B is a plan view of the sterilant injection block 62 of FIG. 14A.

Figure 14C:
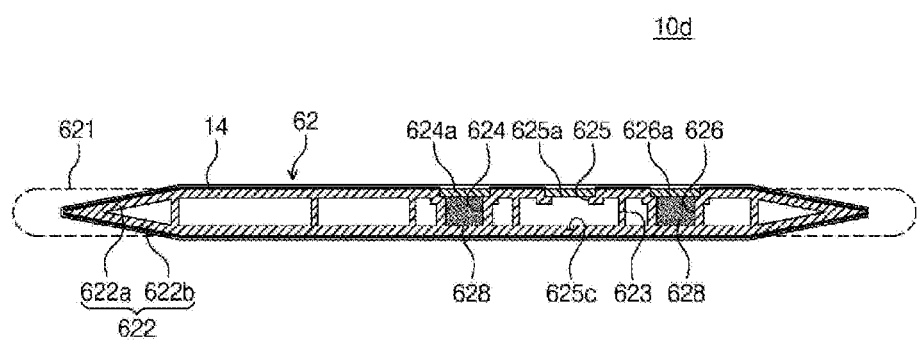
FIGS. 14C and 14D are cross-sectional views of the sterilant injection block 62 of FIG. 14A.
Figure 14D:
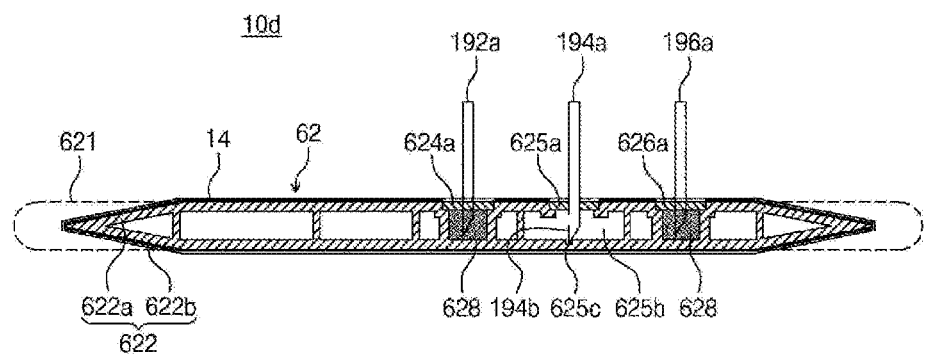

FIGS. 14C and 14D are cross-sectional views of the sterilant injection block 62 of FIG. 14A.

Referring to FIGS. 14A to 14D, a vacuum packaging pouch 10d may include the sterilant injection block 62 for containing an object to be treated therein and being sealed to be in a vacuum state, and vacuum evacuating and injecting a sterilant from the outside.

The sterilant injection block 62 includes: an upper strip 622a and a lower strip 622b having opposite ends bent to contact each other and the central portions extending parallel to each other; a barrier wall 623 between the upper strip and the lower strip; a sterilant injection path 625 formed through the upper strip and opened at the side; a sterilant injection path stopper 625a of an elastic material disposed on the upper strip to block the sterilant injection path; and an alignment strip 621 extending laterally along one side of the upper strip and the lower strip to seal the one side of the upper strip and the lower strip. An upper surface of the upper strip and a lower surface of the lower strip may be thermally compressed at one end of the vacuum packaging pouch.

The sterilant injection path 625 may be supported by a cylindrical guide portion 625b cut in half. In addition, the lower strip 622b may include a main needle alignment portion 625c at a center position of the sterilant injection path 625.

The sterilant injection block 62 may further include: sterilant containers 624 and 626 disposed to be spaced apart from the sterilant injection path 625 and containing the sterilant and being sealed; and sterilant container stoppers 624a and 626a of an elastic material disposed on the upper strip and blocking the sterilant containers 624 and 626. The sterilant container stoppers 624a and 626a may be films or plates of an elastic material such as silicone rubber.

The main needle 194a includes a hole 194b on a side surface of the end of the main needle 194a and may efficiently provide a fluid path. The auxiliary needles 192a and 196a may respectively pass through the sterilant container stoppers 624a and 626a to extract a sterilant.

The purpose of separating a space for a sterilant is to inject the sterilant twice in a sterilization process, and sterilization may be performed twice to increase reliability of the sterilization process. A constant amount of sterilant may be independently controlled for each injection.

A structure of the sterilant containers 624 and 626 spaced apart from each other in a longitudinal direction may supply two independent sterilants to a sterilizer using one cover. An auxiliary needle for extracting a sterilant is primarily connected to the first sterilant container 624, and after primary sterilization is completed, the auxiliary needle is moved and connected to the second sterilant container 626 to perform secondary sterilization.

The embodiments are examples, and thus, it will be understood by those of ordinary skill in the art that various changes in form and details may be made therein without departing from the spirit and scope of the present invention. Therefore, the embodiments should be considered in descriptive sense only and not for purposes of limitation.

The invention claimed is:

1. A sterilization method comprising:
 performing an operation in which a sterilant injection block comprising a sterilant container configured to contain a sterilant or a packaging pouch coupled with the sterilant injection block is mounted in a chamber;
 performing an operation of extracting information from an identification code attached to the sterilant injection block, the identification code being a bar code or a QR code;
 determining whether the extracted information corresponds to a chamber mode or a pouch mode; and
 performing an operation of extracting the sterilant from the sterilant container and injecting the sterilant into the chamber based on determining the information corresponds to the chamber mode or performing an operation of extracting the sterilant from the sterilant container and injecting the sterilant into the packaging pouch based on determining the information corresponds to the pouch mode.

2. The sterilization method of claim 1, wherein the chamber mode comprises:
 evacuating the chamber.

3. The sterilization method of claim 2, wherein the chamber mode further comprises:
 lifting a sterilant extractor to extract the sterilant from the sterilant container.

4. The sterilization method of claim 3, wherein the chamber mode further comprises:
 lifting a main needle; and
 vaporizing the extracted sterilant and injecting the vaporized sterilant into the chamber through the main needle.

5. The sterilization method of claim 4, wherein the chamber mode further comprises:
 lowering the sterilant extractor and the main needle;
 evacuating the sterilant from the chamber; and
 venting the chamber.

6. The sterilization method of claim 1, wherein the pouch mode comprises:
 evacuating the chamber and evacuating the packaging pouch.

7. The sterilization method of claim 6, wherein the pouch mode further comprises:
 lifting a sterilant extractor to extract a sterilant from the sterilant container.

8. The sterilization method of claim 7, wherein the pouch mode further comprises:
 lifting a main needle; and
 vaporizing the extracted sterilant and injecting the vaporized sterilant into the packaging pouch through the main needle.

9. The sterilization method of claim 8, wherein the pouch mode further comprises:
 lowering the sterilant extractor;
 evacuating the sterilant from the packaging pouch through the main needle;
 venting the chamber and venting the packaging pouch using the main needle; and
 lowering the main needle.

* * * * *